US009855239B2

(12) United States Patent
Maeda et al.

(10) Patent No.: US 9,855,239 B2
(45) Date of Patent: *Jan. 2, 2018

(54) METHODS FOR THE TREATMENT AND PREVENTION OF AGE-RELATED RETINAL DYSFUNCTION

(71) Applicant: University of Washington, Seattle, WA (US)

(72) Inventors: Tadao Maeda, Mayfield Heights, OH (US); David Saperstein, Seattle, WA (US); Krzysztof Palczewski, Bay Village, OH (US)

(73) Assignee: University of Washington, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/220,315

(22) Filed: Jul. 26, 2016

(65) Prior Publication Data

US 2016/0331713 A1 Nov. 17, 2016

Related U.S. Application Data

(63) Continuation of application No. 13/619,947, filed on Sep. 14, 2012, now Pat. No. 9,408,821, which is a continuation of application No. 12/368,427, filed on Feb. 10, 2009, now Pat. No. 8,324,270.

(60) Provisional application No. 61/027,625, filed on Feb. 11, 2008.

(51) Int. Cl.
| | | |
|---|---|---|
| *A61K 31/07* | (2006.01) | |
| *A61K 31/215* | (2006.01) | |
| *A61K 31/4709* | (2006.01) | |
| *A61K 31/22* | (2006.01) | |
| *A61K 9/00* | (2006.01) | |

(52) U.S. Cl.
CPC .......... *A61K 31/215* (2013.01); *A61K 9/0053* (2013.01); *A61K 31/07* (2013.01); *A61K 31/22* (2013.01); *A61K 31/4709* (2013.01); *Y10S 514/912* (2013.01)

(58) Field of Classification Search
None
See application file for complete search history.

(56) References Cited

U.S. PATENT DOCUMENTS

| | | |
|---|---|---|
| 3,196,078 A | 7/1965 | Chatzinoff et al. |
| 3,517,067 A | 6/1970 | Stern |
| 5,457,135 A | 10/1995 | Baranowitz et al. |
| 5,620,970 A | 4/1997 | Han et al. |
| 5,837,728 A | 11/1998 | Purcell |
| 5,869,468 A | 2/1999 | Freeman |
| 6,300,328 B1 | 10/2001 | Klimko |
| 6,552,009 B2 | 4/2003 | Achkar |
| 6,696,069 B2 | 2/2004 | Harichian et al. |
| 7,566,808 B2 | 7/2009 | Rando |
| 7,951,841 B2 * | 5/2011 | Palczewski ........... C07C 403/10 514/529 |
| 8,324,270 B2 * | 12/2012 | Maeda ................... A61K 31/07 514/506 |
| 8,962,691 B2 | 2/2015 | Palczewski et al. |
| 9,149,446 B2 | 10/2015 | Palczewski et al. |
| 9,162,978 B2 | 10/2015 | Palczewski et al. |
| 9,169,204 B2 | 10/2015 | Palczewski et al. |
| 9,174,936 B2 * | 11/2015 | Palczewski ........... C07C 403/10 |
| 9,233,091 B2 * | 1/2016 | Maeda ................... A61K 31/07 |
| 9,388,130 B2 * | 7/2016 | Palczewski ........... C07C 403/10 |
| 9,403,765 B2 * | 8/2016 | Palczewski ........... C07C 403/10 |
| 9,408,821 B2 * | 8/2016 | Maeda ................... A61K 31/07 |
| 2002/0028849 A1 | 3/2002 | Godkin et al. |
| 2003/0215413 A1 | 11/2003 | Fares et al. |
| 2003/0228277 A1 | 12/2003 | Gehlsen |
| 2004/0022766 A1 | 2/2004 | Acland et al. |
| 2004/0097587 A1 | 5/2004 | Arbiser |
| 2004/0242704 A1 | 12/2004 | Palczewski et al. |
| 2006/0167088 A1 | 7/2006 | Widder et al. |
| 2006/0281821 A1 | 12/2006 | Palczewski |
| 2008/0221208 A1 | 9/2008 | Palczewski et al. |
| 2008/0275133 A1 | 11/2008 | Schwartz et al. |
| 2010/0035986 A1 | 2/2010 | Maeda et al. |

(Continued)

FOREIGN PATENT DOCUMENTS

| | | |
|---|---|---|
| CA | 2601278 A1 | 9/2005 |
| CN | 1169854 A | 1/1998 |

(Continued)

OTHER PUBLICATIONS

Haimovici et al., Dark adaptation in age-related macular degeneration: relationship to the fellow eye, Graefes Arch Clin Exp Ophthalmol. Feb. 2002;240(2):90-5, printed from https://www.ncbi.nlm.nih.gov/pubmed/11931085, 2 pages.*

Wang et al., "Gene mutations in retinitis pigmentosa and their clinical implications", Clinica Chimica Acta, vol. 351, No. 1-2, pp. 5-16 (2005).

Ablonczy et al., "11-cis-retinyl reduces constitutive phosphorylyzation and improves quantum catch in retinoid-deficient mouse rod photoreceptors", J. Biol. Chem., vol. 277, pp. 40491-40498 (2002).

Acland et al., "Gene therapy restores vision in a canine model of childhood blindness", Nature Genetics, vol. 28, pp. 92-95 (2001).

Acland et al., "Long-term restoration of rod and cone vision by single dose rAAV-mediated gene transfer to the retina in a canine model of childhood blindness", Mol. Ther., vol. 12, No. 6, pp. 1072-1082 (2005).

(Continued)

*Primary Examiner* — Gigi Huang
(74) *Attorney, Agent, or Firm* — Jacqueline F. Mahoney; Judy M. Mohr; McDermott Will & Emery LLP

(57) ABSTRACT

A method of treating or preventing age-related retinal dysfunction involves administering to a patient a pharmaceutically effective amount of a synthetic retinal derivative repeatedly over a duration of at least about 3 months. Effective synthetic retinal derivatives include 9-cis-retinyl esters, 11-cis-retinyl esters, derivatives and congeners thereof, and combinations thereof. Suitable ester substituents include carboxylates of $C_1$-$C_{10}$ monocarboxylic acids and $C_2$-$C_{22}$ polycarboxylic acids.

21 Claims, 9 Drawing Sheets

(56) References Cited

U.S. PATENT DOCUMENTS

| | | |
|---|---|---|
| 2011/0034554 A1 | 2/2011 | Washington |
| 2011/0288170 A1 | 11/2011 | Palczewski et al. |
| 2012/0041073 A1 | 2/2012 | Palczewski et al. |
| 2012/0322891 A1 | 12/2012 | Palczewski et al. |
| 2013/0072443 A1 | 3/2013 | Palczewski et al. |
| 2013/0072556 A1 | 3/2013 | Palczewski et al. |
| 2013/0072557 A1 | 3/2013 | Maeda et al. |
| 2013/0072558 A1 | 3/2013 | Maeda et al. |
| 2013/0072559 A1 | 3/2013 | Palczewski et al. |
| 2013/0072560 A1 | 3/2013 | Palczewski et al. |
| 2013/0072561 A1 | 3/2013 | Maeda et al. |
| 2013/0072568 A1 | 3/2013 | Palczewski et al. |
| 2013/0072569 A1 | 3/2013 | Palczewski et al. |
| 2013/0079403 A1 | 3/2013 | Palczewski et al. |
| 2013/0196950 A1 | 8/2013 | Palczewski et al. |
| 2016/0045453 A1 | 2/2016 | Palczewski et al. |

FOREIGN PATENT DOCUMENTS

| | | |
|---|---|---|
| CN | 1455780 A | 11/2003 |
| CN | 1988898 A | 6/2007 |
| EP | 0803248 A2 | 10/1997 |
| GB | 1449027 | 9/1976 |
| GB | 1526410 A | 9/1978 |
| JP | 61-275266 A | 5/1986 |
| JP | 6340525 A | 12/1994 |
| JP | 8198746 A | 8/1996 |
| RU | 2106843 C1 | 3/1998 |
| WO | WO 96/24344 | 8/1996 |
| WO | WO 99/09969 | 3/1999 |
| WO | WO 99/29315 A | 6/1999 |
| WO | WO 00/68364 A2 | 11/2000 |
| WO | WO 02/055540 A1 | 7/2002 |
| WO | WO 02/058586 A2 | 8/2002 |
| WO | WO 02/066068 A2 | 8/2002 |
| WO | WO 02/082904 A2 | 10/2002 |
| WO | WO 03/059336 A1 | 7/2003 |
| WO | WO 2004/082622 A2 | 9/2004 |
| WO | WO 2005/079774 A2 | 9/2005 |
| WO | WO 2006/002097 A2 | 1/2006 |
| WO | WO 2006/033734 A2 | 3/2006 |

OTHER PUBLICATIONS

Aggarwal et al., "2-Halogeno-1,3-dithiane 1 ,3-dioxide: a diastereoselective carbonyl anion equivalent in reactions with aldehydes", J. Chem. Soc., vol. 1, pp. 11-19 (1997).

Albeck et al., "Factors Affecting the Absorption Maxima of Acidic Forms of Bacteriorhodopsin", Biophys. J., vol. 56, pp. 1259-1265 (1989).

Aleman et al., "Impairment of the transient papillary light reflex in Rpe65(−/−) mice and humans with leber congenital amaurosis", Invest. Opthalmol. Vis. Sci., vol. 45, No. 4, pp. 1259-1271 (2004).

Ames et al., "Biomedical studies on vitamin A. XIV. Biopetencies of Geometric Isomers of Vitamin in the Rat", J. Am. Chem. Soc., vol. 77, pp. 4134-4136 (1955).

Asato et al., "Flourinated rhodopsin analogues from 10-flouro- and 14-flouroretinal", J. Am. Chem. Soc., vol. 100, No. 18, pp. 5957-5960 (1978).

Baehr et al., "The retinoid cycle and retina disease", Vision Research, vol. 43, pp. 2957-2958 (2003).

Batten et al., "Lecithin-retinol acyltransferase is essential for accumulation of all-trans-retinyl esters in the eye and in the liver" The Journal of Biological Chemistry, vol. 279, No. 11, pp. 10422-10432 (2004).

Batten et al., "Pharmacological and rAAV gene therapy rescue of visual functions in a blind mouse model of leber congenital amaurosis", PLoS Medicine, vol. 2, Issue. 11, No. e333, pp. 1177-1189 (2005).

Beischel et al., "Azidotetrafluorophenyl retinal analogue; synthesis and bacteriorhodopsin pigment formation", Photochemistry and Photobiology, vol. 60, No. 1, pp. 64-68 (1994).

Bernstein et al., "Biochemical characterization of the retinoid isomerasa system of the eye", J. Biol. Chem., vol. 262, No. 35, pp. 16848-16857 (1987).

Berson et al., "A randomized trial of vitamin A and vitamin E supplementation for retinitis Pigmentosa", Arch. Opthamol., vol. 111, pp. 761-772 (1993).

Berson et al., "Retinitis pigmentosa: unfolding its mystery", Proc. Natl. Sci. USA, vol. 93, pp. 4526-4528 (1996).

Berson, "Treatment of retinitis Pigmentosa with vitamin A", Digital J. Opthamol., vol. 4, No. 7 Massachusetts Eye and Ear Infirmary, Harvard Medical School (1998).

Berson et al., "Disease progression in patients with dominant retinitis pigmentosa and rhodopsin mutations", Invest. Opthalmol. Vis. Sci., vol. 43, No. 9, pp. 3027-3036 (2002).

Biesalski et al., "Sensitive Analysis of Retinyl Esters by Isocratic Adsorption Chromatography", J. Clin. Chem. Clin. Biochem., vol. 27, No. 2, pp. 65-74 (1989) Abstract only.

Birnbach et al., "Retinoic acid accelerates photoreceptor cell death by apoptosis in Pro23HIS rhodopsin transgenic mice", Invest. Opthalmol. Vis. Sci., vol. 38, No. 4, pp. s311 (1997).

Boehm et al., "Photoaffinity labeling studies of bacteriorhodopsin with [15-$^3$h]-3-Diazo-4-keto-all-trans-retinal", J. Am. Chem. Soc., vol. 112, pp. 7779-7782 (1990).

Borhan et al., "Chemoenzymatic synthesis of 1-cis-retinal photoaffinity analog by use of squid retinochrome", J. Am. Chem. Soc., vol. 119, pp. 5758-5759 (1997).

Borhan et al., "Efficient synthesis of 11-cis-retinoids", Chem. Eur. J., vol. 6, No. 4, pp. 1172-1175 (1999).

Bridges, "Vitamin A* and the Role of the Pigment Epithelimn during Bleaching and Regeneration of Rhodopsin in the Frog Eye", Exp. Eye Res., vol. 22, pp. 435-455 (1976).

Brogan et al., "Altered retinoid homeostasis catalyzed by a nicotine metabolite: implications in macular degeneration and normal development", Proc. Natl. Acad. Sci. USA, vol. 102, No. 30, pp. 10433-10438 (2005).

Buczylko et al., "Mechanisms of opsin activation", J. Biol. Chem., vol. 271, No. 34, pp. 20621-20630 (1996).

Caldwell et al, "Synthesis of retinals with eight- and nine-membered rings in the side chain, models for rhodopsin photobleaching intermediates", J. Org. Chem., vol. 58, pp. 3533-3537 (1993).

Capecchi, "Altering the genome by homologous recombination", Science, vol. 244, No. 4910, pp. 1288-1292 (1989).

Carney and Russell, "Correlation of Dark Adaptation Test Results with Serum Vitamin A Levels in Diseased Adults", J. Nutr., vol. 110, pp. 552-557 (1980).

Caruso et al, "Effects of fenretinide (4-HPR) on dark adaptation", XP002475887; STN Database Accession No. 1998:418096 & Archives of Ophthalmology (Chicago), vol. 116, No. 6, pp. 759-763, Coden: AROPAW; ISSN:0003-9950, (1998) Abstract only.

Chan et al., "Delayed dark adaption cause by nilutamide", J. Neuro-Opthalmology, vol. 28, No. 2, pp. 158-159 (2008).

Chapple et al., "Looking at protein misfolding neurodegenerative disease through retinitis pigmentosa", ACNR, vol. 3, Issue 1, pp. 12-13 (2003).

Chatzinoff et al., "Eleven-cis vitamin A in the treatment of retinitis Pigmentosa", Arch. Opthalmol., vol. 80, pp. 417-419 (1968).

Chen et al., "Inherent instability of the retinitis pigmentosa P23H mutant opsin", JBC Papers in Press, Manuscript M114.551713, 31 pages, Latest version can be accessed at http://www.jbc.org/cgi/doi/10.1074/jbc.M114.551713, Published Feb. 10, 2014.

Cideciyan et al., "Rod and cone visual cycle consequences of a null mutation in the 11-cis-retinol dehydrogenase gene in man", Vis. Neurosci., vol. 17, No. 5, pp. 667-678 (2000).

Colmenares et al., "11,12-Difluororhodopsin and related odd-numbered fluororhodopsins, the use of $J_{F,F}$ for following a cis-trans isomerization process", J. Am. Chem. Soc., vol. 121, pp. 5803-5804 (1999).

Congdon et al., "Responsiveness of dark-adaptation threshold to vitamin A and β-carotene supplementation in pregnant and lactating women in Nepal", Am. J. Clin. Nutr., vol. 72, pp. 1004-1009 (2000).

Corson et al., "Sensititzation of bleach rod photoreceptors by 11-cis-locked analogues of retinal", PNAS USA, vol. 87, pp. 6823-6827 (1990).

(56) References Cited

OTHER PUBLICATIONS

Crescitelli and Pearlman, "Can isorhodopsin be produced in the living rat?", Vision Res., vol. 13, pp. 2515-2525 (1973).
Crescitelli et al., "The spectral properties and photosensitivies of analogue photopigments regenerated with 10- and 14-substituted retinal analogues" Proc. R. Soc. Lond. B, vol. 233, pp. 55-76 (1988).
Crouch et al., "Photo sensitive pigments formed with rat opsin", Invesitgative Opthalmology, vol. 15, No. 10, pp. 872-875 (1976).
Crouch and Katz, "The effect of retinal isomers on the ver and erg of vitamin A deprived rats", Vision Res., vol. 31, pp. 109-115 (1980).
Crouch et al., "Inhibition of rhodopsin regeneration of cyclohexyl derivatives", Vision Research, vol. 22, No. 12, pp. 1451-1466 (1982).
Crouch et al., "Opsin pigments formed with acyclic retinal analogues", FEBS, vol. 158, No. 1, pp. 139-142 (1983).
Crouch et al., "Cycloheptatrienylidene analog of 11-cis retinal", Invest. Opthalmol. Vis. Sci., vol. 25, pp. 419-428 (1984).
Crouch, "Yearly review: studies of rhodopsin and bacteriorhodopsin using modified retinals", Photochemistry and Photobiology, vol. 44, No. 6, pp. 803-807 (1986).
De Grip et al., "10 20 methanorhodopsins 7e 9e 13e-10 20 mthanorhodopsin and 7e 9z 13z-10 20 methanorhodopsin 11-cis-locked rhodopsin analog pigments with unusual thermal and photostability", Eur. J. Biochem., vol. 191, No. 1, pp. 211-220 (1990).
Delange et al., "An additional methyl group at the 10-position of retinal dramatically slows down the kinetics of the rhodopsin photocascade", Biochemistry, vol. 37, No. 5, pp. 1411-1420 (1998).
Dorwald, *Side Reactions in Organic Synthesis: A Guide to Succesful Synthesis Design*, Wiley-VCH Verlag GmbH & Co. KGaA, Weinheim, Preface p. XI, (2005).
Drachev et al., "An invesitgation of the electrochemical cycle of bacteriorhodopsin analgogs with the modified ring", Arch. Biochem. Biophys., vol. 270, No. 1, pp. 184-197 (1989).
Driessen et al., "Disruption of the 11-cis-retinol dehydrogenase gene leads to accumulation of cis-retinols and cis-retinyl esters", Mol. Cell Biol., vol. 20, No. 12, pp. 4275-4287 (2000).
Ebrey et al., "Properties of several sterically modified retinal analogs and their photosensitive pigments", Biochemistry, vol. 14, No. 18, pp. 3933-3941 (1975).
European Search Report From related European Patent Application No. EP 04757476, dated Jun. 5, 2008.
European Search Report From Related European Patent Application No. 1154402, search completed on Sep. 5, 2011.
European Search Report From Related European Patent Application No. EP 1154404, search completed on Sep. 6, 2011.
European Search Report From Related European Patent Application No. EP 1154534, search completed on Sep. 5, 2011.
Eyring el al., "Assignment and interpretation of hydrogen out-of-plane vibrations in the resonance raman spectra of rhodopsin and bathorhodopsin", Biochemistry, vol. 21, pp. 384-393 (1982).
Fan et al., "Isorhodopsin rather than rhodopsin mediates rod function in RPE65 knock-out mice" PNAS, vol. 100, No. 23, pp. 13662-13667 (2003).
Fujimoto et al., "On the bioactive conformation of the rhodopsin chromophore: absolute sense of twist around the 6-s-cis bond", Chem. Eur. J., vol. 7, No. 19, pp. 4198-4204 (2001).
Fujimoto et al., "Solution and biologically relevant conformations of enantiomeric 11-cis-locked cyclopropyl retinals", J. Am. Chem. Soc., vol. 124, pp. 7294-7302 (2002).
Fukada et al., "Studies on structure and function of rhodopsin by use of cyclopenatrienylidene 11-cis-locked rhodopsin", Biochemistry, vol. 23, No. 24, pp. 5826-5832 (1984).
Futterman et al., "The composition of liver vitamin A ester and the synthesis of vitamin A ester by liver microsomes", J. Biol. Chem., vol. 239, No. 12, pp. 4077-4080 (1964).
Gaffney et al., "Aging and cone dark adaptation", Optom. Vis. Sci., vol. 89, No. 8, pp. 1219-1224 (2012).

Gao and Hollyfield, "Aging of the human retina" Inv. Opth. Vis. Sci., vol. 33, pp. 1-17 (1992).
Gartner et al., "Quantum yield to chapso-solubilized rhodopsin and 3-hydroxy retinal containing bovine opsin", Photochemistry and Photobiology, vol. 54, No. 6, pp. 1047-1055 (1991).
Geroski et al., "Durg delivery for posterior segment eye disease", IOVS, vol. 41, No. 5, pp. 961-964 (2000).
Grant et al., "Treatable forms of retinitis pigmentosa associated with systemic neurological disorders", Int. Opthalmol. Clin., vol. 41, No. 1, (2001) printed from http://www.ncbi.nim.nih.gov/pubmed/11198137 on Jan. 14, 2009 Abstract only.
Haeseleer et al., "Dual-substrate specifically short chain retinol dehydrogenases from the vertebrate retina", J. Biol. Chem., vol. 277, No. 47, pp. 45537-46546 (2002).
Haig et al., "Vitamin A and Rod-Cone Dark Adaption in Cirrhoses of the Liver", Science, vol. 87, No. 2267, pp. 534-536 (1938).
Han et al., "The C9 methyl group of retinal interacts with glycine-121 in rhodopsin", PNAS, vol. 94, pp. 13442-13447 (1997).
Harvard Health Publications, "The aging eye: preventing and treating eye disease", Harvard Helath Publications, 3 pgs. (2011) printed from http://www.health.harvard.edu/special_health_reports/the_Aging_Eye on Nov. 5, 2011.
Head, "Natural therapies for ocular disorders, part one: diseases of the retina", Alt. Med. Review, vol. 4, No. 5, pp. 342-359 (1999).
Hiraki et al., "Bacteriorhodopsin analog regenerated with 13-desmethyl-13-lodoretinal", Biophysical Journal, vol. 83, pp. 3460-3469 (2002).
Hirano et al., "Constraints of opsin structure on the ligand-binding site: studies with ring-fused retinals", Photochemistry and Photobiology, vol. 76, No. 6, pp. 608-615 (2002).
Hisatomi et al., "Critical role of photoreceptor apoptosis in functional damage after retinal detachment", Curr. Eye Res., vol. 24, No. 3, 161-172 (2002) Abstract only, 1 pg., printed from http://www.ncbi,nim.nih.gov/pubmed/12221523.
Howard et al., "Comparative distribution, pharmacokinetics and placental permeabilities of all-trans-retinoic acid, 13-cis-retinoic acid, all-trans-4-oxo-retinoic acid, retinyl acetate and 9-cis-retinal in hamsters", Arch. Toxicol., vol. 63, pp. 112-120 (1989).
Hu et al., "Unbleachable rhodopsin with an 11-cis-locked eight-membered ring retinal: the visual transduction process", Biochemistry, vol. 33, pp. 408-416 (1994).
Huttunen et al., "Prodrugs—from Serendipity to Rational Design", Pharmacological Reviews, vol. 63, No. 3, pp. 750-771 (2011).
Illing et al., "A Rhodopsin mutant linked to autosomal dominant retinitis pigmentosa is prone to aggregate and interacts with ubiquitin proteasome system", J. Biol. Chem., vol. 277, No. 37, pp. 34150-34160 (2002).
Imai et al., "Probing for the threshold energy for visual transduction: red-shifted visual pigment analogs from 3-methoxy-3-dehydroretinal and related compounds", Photochemistry and Photobiology, vol. 70, No. 1, pp. 111-115 (1999).
Imamoto et al., "Structure around $C_6$—$C_7$ bond of the chromophore in bathorhodopsin: low-temperature spectroscopy of 6s-cis-locked bicycle rhodopsin analogs", Biochemistry, vol. 35, pp. 6257-6262 (1996).
Imanishi et al., "Noninvasive two-photon imaging reveals retinyl ester storage structures in the eye", Cell Biol. vol. 164, pp. 373-383 (2004).
International Search Report from related PCT Patent Application No. PCT/US2004/007987 dated Dec. 3, 2004, application now published as International Publication No. WO2004/082622, published on Sep. 30, 2004.
International Search Report from related PCT Patent Application No. PCT/US2005/021812 dated Dec. 28, 2005, application now published as International Publication No. WO2006/002097, published on Jan. 5, 2006.
International Search Report from related PCT Patent Application No. PCT/US2009/000824 dated Nov. 5, 2009, application now published as International Publication No. WO2009/102418, published on Aug. 20, 2009.
Jackson et al., "Aging and scotopic sensitivity", Vis. Res., vol. 38, pp. 3655-3662 (1998).

(56) References Cited

OTHER PUBLICATIONS

Jackson et al., "Aging and dark adaption", Vis. Res. vol. 39, pp. 3975-3982 (1999).
Jackson et al., "Photoreceptor degeneration and dysfunction in aging and age-related maculopathy", Aging Res. Rev., vol. 1, No. 3, pp. 381-396 (2002).
Jacobson et al., "Retinal degenerations with truncation mutations in the cone-rod homeobox (CRX) gene", Invest. Opthalmol. Vis. Sci., vol. 39, No. 12, pp. 2417-2426 (1988).
Jacobson et al., "Night blindness is Sorsby's fundus dystrophy reversed by vitamin A" Nat. Genet. vol. 11, pp. 27-32 (1995).
Jacobson et al., "Phenotypic Marker for Early Disease Detection in Dominant Late-Onset Retinal Degeneration", IOVS, vol. 42, No. 8, pp. 1882-1890 (2001).
Jacobson et al., "Identifying photoreceptors in blind eyes caused by RPE65 mutations: Prerequisite for human gene therapy success", PNAS USA, vol. 102, No. 17, pp. 6177-6182 (2005).
Jang, "Mechanism of rhodopsin acvtivation as examined with ring-constrained retinal analogs and the crystal structure of the ground state protein", The Journal of Biological Chemistry, vol. 276, No. 28, pp. 26148-26153 (2001).
Jang et al., "Characterization of a dehydrogenase activity responsible for oxidation of 11-cis-retinal in the retinal pigment epithelium of mice with a disrupted RDH5 gene. A model for the human heredity disease fundus albunctatus", J. Biol. Chem., vol. 276, No. 35, pp. 32456-32465 (2001).
Jin et al., "Noncovalent occupancy of the retinal-binding pocket of opsin diminishes bleaching adaption of retinal cones", Neuron, No. 11, pp. 513-522 (1993).
Karnaukhova et al., "Bioactivity of visual pigments with sterically modified retinal analogs", Bioorganic Chemistry, vol. 27, pp. 372-382 (1999).
Kefalov et al., "Role of nocovalent binding of 11-cis-retinal opsin in dark adaption of rod and cone photoreceptors", Neuron, vol. 29, Issue 3, pp. 749-755 (2001).
Kemp et al., "Visual Function and Rhodopsin Levels in Humans with Vitamin A Deficiency", Exp. Eye Res., vol. 46, pp. 185-197 (1988).
Kirillova et al., "Cyclopentene and cyclohexene retinal analogs react differently with bacterioopsin", Chemical Abstracts, vol. 120, pp. 557, (1994) Abstract No. 128:187138 Abstract only.
Koenekoop et al., "Oral 9-cis retinoid for childhood blindness due to Leber congenital amaurosis caused by RPE65 or LRAT mutations: an open-label phase 1b trial", Lancet, 8 pages, Published Online http://dx.doi.org/10.1016/S0140-6736(14)60153-7, Published Jul. 14, 2014.
Kubo et al., "Effect of vitamin A palmitate on vitamin A-deficient rabbits", XP002475885; STN Database Accession No. 2000:172779 & Nippon Ganka Gakkai Zasshi, vol. 103, No. 10, pp. 729-733 Coden:NGZAA6; ISSN: 0029-0203, 1999 Abstract only.
Kuska et al., "Biochemical and physiological properties of rhodopsin regenerated with 11-cis-6-ring- and 7-ring-retinals", The Journal of Biological Chemistry, vol. 277, No. 44, pp. 42315-42324 (2002).
Kuksa et al., "Retinoid cycle in the vertebrate retina: experimental approaches and mechanisms of isomerization", Vision Research, vol. 43, pp. 2959-2961 (2003).
Kupfer et al., "Information for doctors who follow patients with retinitis pigmentosa", National Eye Institute (1993), printed from http://www.nei.nih.gov/news/clinicalalerts/alert-rp.asp on Jan. 15, 2009, 2 pages.
Kuse et al., "Change in rod cell function by age-related macular degeneration", Japanese Review of Clinical Ophthalmology, vol. 10, No. 100, pp. 59 (2006) English Abstract.
Lamb and Pugh, "Dark adaption and the retinoid cycle of vision", Prog. Retin. Eye Res., vol. 23, pp. 307-380 (2004).
Lamb and Pugh, "Phototransduction, Dark Adaptation, and Rhodopsin Regeneration", IOVS, vol. 47, No. 12, pp. 5138-5152 (2006).

Lang, "Ocular drug delivery conventional ocular formulations", Adv. Drug Del. Rev., vol. 16, No. 1, pp. 39-43 (1996).
Lawson et al., "Retinal analog restoration of photophobic responses in a blind chlamydomonas-reinhardtll mutant evidence for an archaebaterial like chromophore in a eukaryotic rhodopsin", Biophysical Journal, vol. 60, No. 6, pp. 1490-1498 (1991).
Lewin et al., "Synthesis and characterization of trans-, 13-cis-, and 11-cis, 13-cis-12-(hydroxymethyl)retinols", J. Org. Chem., vol. 49, pp. 649-652 (1984).
Lewis et al., "Steric barrier to bathorhodopsin decay in 5-demethyl and mesityl analogues of modopsin", J. Am. Chem. Soc., vol. 123, pp. 10024-10029 (2001).
Li et al., "Effect of vitamin A supplementation on rhodopsin mutants threonine-17→methionine and proline-347→serine in transgenic mice and in cell cultures", Proc. Natl. Acad. Sci. USA, vol. 95, pp. 11933-11938 (1998).
Li et al., "Delivery of 9-cis retinal of photoreceptors from bovine serum albumin", Photochem. Photobiol., vol. 69, No. 4, pp. 500-504 (1999).
Lin et al., "Vibrational Assignment of Torsional Normal Modes of Rhodopsin: Probing Excited-State Isomerization Dynamics along the Reaction $C_{11}$—$C_{12}$ Torsion Coordinate", J. Phys. Chem. B, vol. 102, pp. 2787-2806 (1998).
Liu et al., "The nature of restriction in the binding site of rhodopsin. A model study", J. Am. Chem. Soc., vol. 106, No. 26, pp. 8298-8300 (1984).
Maeda et al., "Evaluation of the role of the retinal g protein-coupled receptor (RGR) in the vertebrate retina in vivo", Journal of Neurochemistry, vol. 85, pp. 944-956 (2003).
Maeda et al., "Improvement in Rod and Cone Function in Mouse Model of *Fundus albipunctatus* after Pharmacologic Treatment with 9-cis-Retinal", IOVS, vol. 47, No. 10, pp. 4540-4546 (2006).
Maeda et al., "Effects of long-term administration of 9-cis-retinyl acetate on visual function in mice", Inv. Opth. Vis. Sci., vol. 50, No. 1, pp. 322-332 (2009).
Maeda et al., "QLT091001, a 9-cis-retinal analog, is well-tolerated by retinas of mice with impaired visual cycles", Invest. Opthalmol. Vis. Sci., vol. 54, No. 1, pp. 455-466 (2013).
Marmor et al., "Abipunctate retinopathy with cone dysfunction and no abnormality in RDH5 or RLBP1 genes", Retina, vol. 23, No. 4, pp. 543-546 (2003).
Massoud et al., "Plasma vitamin A and beta-carotene in retinitis pigmentosa", Brit. J. Opthal., vol. 59, pp. 200-204 (1975).
Mata et al., "Substrate specificity of retinyl ester hydrolase activity in retinal pigment epithelium", Journal of Lipid Research, vol. 39, pp. 604-612 (1998).
Matsukawa et al., "Role of purpurin as a retinal-binding protein in goldfish retina during the early stage of optic nerve regeneration: Its priming action on neurite outgrowth", J. Neurosci., vol. 24, No. 38, pp. 8346-8353 (2004).
Maugard et al., "Enzymatic synthesis of derivatives of vitamin A in organic media", J. Mol. Cat. B, vol. 8, pp. 275-280 (2000).
Maugard et al., "Synthesis of water-soluble retinol derivatives by enzymatic method", Biotechnol. Prog. vol. 18, pp. 424-428 (2002).
Maxwell et al., "Photodynamic responses in rhodotorula glutins in the absence of added sensitizers", Photochemistry and Photobiology, vol. 13, No. 3, pp. 259-273 (1971).
Mayo Clinic, "Retinal detachment", 8 pgs. (2010) printed from http://www.mayoclinic.com/health/retinal-detachment/DS00254/METHOD=print&DSECTION=all.
McBee et al., "Isomerization of 11-cis-retinoids to all-trans-retinoids in vitro and in vivo", J. Biol. Chem., vol. 276, No. 51, pp. 48483-48493 (2001).
McBee et al. "Confronting complexity: the interlink of phototransduction and retinoid metabolism in the vertebrate retina", Prog. Ret. Eye Res., vol. 20, No. 4, pp. 469-529 (2001).
MedlinePlus, "Diabetic retinopathy", 5 pgs. (2011) printed from http://www.nim.nih.gov/medlineplus/ency/article/00212.htm.
Mendes et al., "Pharmacological manipulation of rhodopsin retinitis pigmentosa", Advances in Experimental Medicine and Biology, Chapter 36, pp. 317-323, DOI 10.1007/978-1-4419-1399-9_36, Springer Science+Business Media, LLC (2010).

(56) References Cited

OTHER PUBLICATIONS

Mizukami et al., "Photoisomerization mechanism of the rhodopsin chromophore: picosecond photolysis of pigment containing 11-cis-locked eight-membered ring retinal", PNAS, vol. 90, pp. 4072-4076 (1993).
Morimura et al., "Mutations in the RPE65 gene in patients with autosomal recessive retinitis pigmentosa or Leber congenital amaurosis", PNAS USA, vol. 95, pp. 3088-3093 (1998).
Nakamura et al., "A high association with cone dystrophy in fundus albipunctatus caused by mutations of the RDH5 gene", Invest. Opthalmol. Vis. Sci., vol. 41, No. 12, pp. 3925-3932 (2000).
Newton et al., "Structure-Activity Relationships of Retinoids in Hamster Tracheal Organ Culture", Cancer Res., vol. 40, pp. 3413-3425 (1980).
Nishiguchi et al., "A novel mutation (I143NT) in guanylate cyclase-activating protein 1 (GCAP1) associated with autosomal dominant cone degeneration", Invest. Opthalmol. Vis. Sci., vol. 45, No. 11, pp. 3863-3870 (2004).
Noell, "Suitability of retinol, retinal and retinyl palmitate for the regeneration of bleached rhodopsin in the isolated frog retina", XP002486105, STN Database Accession No. 1985:164043 & Vision Research, vol. 24, No. 11, pp. 1615-1622, Coden:VISRAM; ISSN:0042-6989, (1984) Abstract only.
Noorwez et al., "Pharmacological chaperone-mediated in vivo folding and stabilization of the P23H-opsin mutant associated with autosomal dominant retinitis Pigmentosa", J. Biol. Chem., vol. 278, No. 16, pp. 14442-14450 (2003).
Noorwez et al., "Retinoids assist the cellular folding of the autosomal dominant retinitis Pigmentosa opsin mutant P23H", J. Biol. Chem., vol. 279, No. 16, pp. 16278-16284 (2004).
Norum and Blomhoff, "McCollum Award Lecture, 1992: Vitamin A absorption, transport, cellular uptake, and storage", Am. J. Clin. Nutr., vol. 56, pp. 735-744 (1992).
O'Byrne et al., "Retinoid adsorption and storage is impaired in mice lacking lecithin: retinol acyltransferase (LRAT)", J. Biol. Chem., vol. 280, pp. 35647-35657 (2005).
Ohgane et al., "Retinobenzaldehydes as proper-trafficking inducers of folding-defective p23H rhodopsin mutant responsible for retinitis pigmentosa", Bioorg. Med. Chem., vol. 18, No. 19, pp. 7022-7028 (2010).
Owsley et al., "Delays in rod-mediated dark adaption in early age-related maculopathy", Ophthalmology, vol. 108, pp. 1196-1202 (2001).
Owsley et al., "Effect of short-term, high-dose retinol on dark adaption in agingand early age-related maculopathy", Invest. Ophthalmol. Vis. Sci., vol. 47, No. 4, pp. 1310-1318 (2006).
Paik et al., "9-cis-retinoids: biosynthesis of 9-cis-retinoic acid", Biochemistry, vol. 39, No. 27, pp. 8073-8084 (Jul. 2000) Abstract only.
Parry et al., "Visual pigment reconstitution in intact goldfish retina using synthetic retinaldehyde isomers", Vision research, vol. 40, No. 17, pp. 2241-2247 (2000).
Perusek and Maeda, "Vitamin A Derivatives as Treatment Options for Retinal Degenerative Disease", Nutrients, vol. 5, pp. 2646-2666 (2013).
Price et al., "Mislocation and degradation of human P23H-Rhodopsin-GFP in a knockin mouse model of retinitis pigmentosa", Inv. Opth. Vis. Sci., vol. 52, No. 13, pp. 9728-9736 (2011).
Radomska et al., "The use of some ingredients for microemulsion preparation containing retinol and its esters", XP002475886, STN Database Accession No. 2000:139945 & International Journal Of Pharmaceutics, vol. 196, No. 2, pp. 131-134 Coden:IJPHDEI: ISSN: 0378-5173, (2000) Abstract only.
Rao et al., "Isomers of 3 7 11 trimethyldodeca-2 4 6 8 10-pentaenal A linear of retinal and lower homologues in the interaction with bovine opsin and bacterioopsin", Photochemistry and Photobiology, vol. 41, No. 2, pp. 171-174 (1985).
Rao et al., "5-(Trifluoromethyl)bacteriorhodopsin does not translocate protons", J. Am. Chem. Soc., vol. 108, pp. 6077-6078 (1986).

Rao et al., "Regioselective photo isomerisation of retinolacetate" Tetrahedron Letters, vol. 31, No. 24, pp. 3441-3444 (1990).
Redmond et al., "Rpe65 is necessary for production of 11-cis-vitamin A in the retinal visual cycle", Nature Genetics, vol. 20, pp. 344-351 (1998).
Reid et al., "Mass Spectral Analysis of Eleven Analogs of Vitamin A1", Lipds, vol. 8, No. 1, pp. 558-565 (1973).
Remington: The Science and Practice of Pharmacy, 19$^{th}$ Edition, Gennaro et al., Ed., Mack Publishing Company, pp. 1528-1529 (1995).
Renk, "A rhodopsin pigment containing a spin-labeled retinal" J. Am. Chem. Soc., vol. 109, pp. 6163-6168 (1987).
Rezabek et al., "Effect of dietary retinyl acetate on the promotion of hepatic enzyme-altered foci by polybrominated biphenyls in initiated rats", Food Chem. Toxicol., vol. 27, No. 8, pp. 539-544 (1989) Abstract only.
Robinson et al., "Opsins with mutations at the site of chromophore attachment constitutively activate transducin but are not phosphorylated by rhodopsin kinase", Proc. Natl. Acad. Sci. USA, vol. 91, No. 12, pp. 5411-5415 (1994).
Rotenstreich et al., "Treatment of a retinal dystrophy, fundus albipunctatus, with oral 9-cis-b-carotene", Br. J. Opthalmol., vol. 94, pp. 616-621 (2010).
Rotenstreich et al., "Treatment with 9-cis β-carotene-rich powder in patients with retinitis pigmentosa: a randomized crossover trial", JAMA Ophthalmol., vol. 181, No. 8, pp. 985-992 (2013).
Russell, "The vitamin A spectrum: from deficiency to toxicity", Am. J. Clin. Nutr., vol. 71, pp. 878-884 (2000).
Sakami et al., "Probing mechanisms of photoreceptor degeneration in a new mouse model of the common form of autosomal dominant retinitis pigmentosa due to P23H opsin mutations", JBC Papers in Press, Manuscript M110.209759, 29 pages, Latest version can be accessed at http://www.jbc.org/cgi/doi/10.1074/jbc.M110.209759, Published Jan. 11, 2011.
Saliba et al., "The cellular fat of mutant rhodopsin: quality control, degradation and aggresome formation", J. Cell Science, vol. 115, pp. 2907-2918 (2002).
Sandberg et al., "Clinical expression correlates with location of rhodopsin mutation in dominant ratinitis Pigmentosa", Invest. Opthalmol. Vis. Sci., vol. 36, No. 9, pp. 1934-1942 (1995).
Sekiya et al., "Effect of modification of the chromophore in retinochrome" Biophysical Chemistry, vol. 56, pp. 31-39 (1995).
Semenova et al., "Systems for delivery of vitamin A to the retina in retinitis pigmentosa", XP002475884; STN Database Accession No. 2002:438129 & New Insights Into Retinal Degenerative Diseases, [Proceedings Of The International Symposium On Retinal Degeneration], 9TH, Durango, Co, United States, (2000), Meeting Date (2000), pp. 105-110; Editor (Anderson & Lavail), (2001) Abstract only.
Semenova et al., "Stabilization of all-trans-retinol by cyclodextrins: a comparative study using HPLC and fluorescence spectroscopy", XP002475883; STN Database Accession No. 2003:494986 & Journal Of Inclusion Phenomena And Macrocyclic Chemistry, Volume Date (2002), vol. 44, No. 1-4, pp. 155-158 Coden:JIPCF5; ISSN:1388-3127, (2003) Abstract only.
Semple-Rowland et al., "A null mutation in the photoreceptor guanylate cyclase gene causes the retinal degeneration chicken phenotype", Proc. Natl. Acad. Sci. USA, vol. 95, No. 3, pp. 1271-1276 (1998).
Sen et al., "Synthesis and binding studies of a photoaffinity label for bovine rhodopsin", J. Am. Chem. Soc., vol. 104, pp. 3214-3216 (1982).
Sibulesky et al., "Safety of <7500 RE (<25000 IU) vitamin A daily in adults with retinitis Pigmentosa", Am. J. Clin. Nutr., vol. 69, pp. 656-663 (1999).
Sokal et al., "GCAP1 (Y99C) mutant is constitutively active in autosomal dominant cone dystrophy", Mol. Cell. vol. 2, No. 1, pp. 129-133 (1998).
Spaeth, "Ophthalmic Surgery: Principles & Practice, Second Edition", Harcourt Brace Jovanich, Inc., pp. 85-99 (1990).

(56) References Cited

OTHER PUBLICATIONS

Stecher et al., "Preferential release of 11-cis-retinol from retinal pigment epithelial cells in the presence of cellular retinaldehyde-binding protein" The Journal of Biological Chemistry, vol. 274, No. 13, pp. 8577-8585 (1999).
Steinberg et al., "Isomer composition and spectra of the dark and light adapted forms of artificial bacteriorhodopsins", Photochemistry and Photobiology, vol. 54, No. 6, pp. 969-976 (1991).
Supplementary European Search Report From Related European Patent Application No. EP 05773576, dated Aug. 4, 2008.
Tan et al., "Absoloute sense of twist of the C12—C13 bond of the retinal chromophorein bovine rhodopsin based of exciton-coupled CD spectra of 11, 12-dihydroretinal analogues", Agnew. Chem. Int. Ed. Engl. vol. 36, No. 19, pp. 2089-2093 (1997).
Tarkhov et al., "Study of a structure-property relationship for retinal derivatives taking into account their conformational flexibility", Chemical Abstracts, vol. 12B, No. 18, pp. 270 (1998) Abstract No. 128:214600 Abstract only.
Teller et al., "Advances in determination of a high-resolution three-dimensional structure of rhodopsin, a model of G-protein-coupled receptors (GPCRs)", Biochemistry vol. 40, No. 26, pp. 7761-7772 (2001).
The Eye Digest, "Aging eye in the US", 2 pgs. (2011) printed from http://web.archive.org/web/20060810014820/http://www.agingeye.net/mainnews/usaging.php.
Thomson Scientific, London, GB; AN 1995-063773, XP002475888 & JP 06340525 A (Lion Corp); Dec. 13, 1993 Abstract only.
Thomson Scientific, London, GB; AN 1996-408307, XP002475889 & JP 08198746 A (Lion Corp); Aug. 6, 1996 Abstract only.
Thomson Scientific, London, GB; AN 1998-518867, XP002475890 & RU 2106843 C1 (Krasy Med Acad); Mar. 20, 1998 Abstract only.
Thompson et al., "Mutations in the gene encoding lecithin retinol acyltransferase are associated with early-onset severe retinal dystrophy", Nat. Genet., vol. 28, pp. 123-124 (2001).
Thompson et al., "Gene defects in vitamin A metabolism of the retinal pigment epithelium", Genetics in Ophthalmology, vol. 37, pp. 141-154 (2003).
Travis et al., "Diseases caused by defects in the visual cycle: retinoids as potential therapeutic agents", Annu. Rev. Pharmacol. Toxicol., vol. 47, pp. 469-512 (2007).
"Types of AMD", Macular Degeneration Partnership, 8733 Beverly Blvd., Suite201, Los Angeles, CA 90048, Online article downloaded from: http://web.archive.org/web/20030216034002/http://www.amd.org/amd/typesofamd.asp, 3 pages (2003).
Van Hooser et al., "Rapid restoration of visual pigment and function with oral retinoid in a mouse model of childhood blindness", PNAS, vol. 97, No. 15, pp. 8623-8628 (2000).
Van Hooser et al., "Recovery of visual functions in a mouse model of leber congenital amaurosis", The Journal of Biological Chemistry, vol. 277, No. 21, pp. 19173-19182 (2002).
Vitamin Converter, Known vitamin A conversion, 3 pgs., printed from http://www.robert-forbes.com/resources/vitaminconverter.html on Apr. 19, 2012.

Wada et al., "Retinoids and related compounds, part 26. synthesis of (11Z)-8,18- propano- and methano-retinals and conformational study of the rhodopsin chromophore", J. Chem. Soc., vol. 1, pp. 2430-2439 (2001).
Weiser and Somorjai, "Bioactivity of cis and dicis isomers of vitamin A esters", Internatl. J. Vit. Nutr., vol. 62, pp. 201-208 (1992).
"What is AMD?", Macular Degeneration Partnership, 8733 Beverly Blvd., Suite201, Los Angeles, CA 90048, Online article downloaded from: http://web.archive.org/web/20030206231257/http://amd.org/amd/index.asp, 2 pages (2003).
Wingerath et al., "Analysis of cyclic and acyclic analogs of retinol, retinoic acid, and retinal by laser desorption Ionization-, matrix-assisted laser desorption ionization-mass spectrometry, and UV/Vis spectroscopy", Analytical Biochemistry, vol. 272, pp. 232-242 (1999).
Witkovsky et al., "Formation, conversion, and utilization of isorhodopsin, rhodopsin, and porphyropsin by rod photoreceptors in the xenopus retina", J. Gen. Physiol., vol. 72, pp. 821-836 (1978).
www.wrongdiagnosis.com, "Symptom: night blindness", pp. 1-13 (Jun. 3, 2008).
Woodward et al., "The inflow and outflow of anti-glaucoma frugs", Trends Pharm. Sci., vol. 25, Issue 5, pp. 238-241 (2004).
Yamamoto et al., "Important role of the proline residue in the signal sequence that directs the secretion of human lysozyme in *Saccharomyces cerevisiae*", Biochemistry, vol. 28, pp. 2728-2732 (1989).
Yamamoto et al., "Mutations in the gene encoding 11-cis retinol dehydrogenase cause delayed dark adaptation and fundus Albipunctatus", Nat. Genet., vol. 22, No. 2, pp. 188-191 (1999).
Yan et al., "Mechanism of activation of sensory rhodopsin I: evidence for a steric trigger", PNAS, vol. 88, pp. 9412-9416 (1991).
Yoshikami et al., "Visual pigments of vitamin A-deficient rat following vitamin A2 administration", Vision Research, vol. 9, No. 6, pp. 633-646 (1969).
Yoshizawa and Wald, "Photochemistry of Iodopsin", Nature vol. 214, pp. 566-571 (1967).
Zankel et al., "Bovine rhodopsin with 11-cis-locked retinal chromophore neither activates rhodopsin kinase nor undergoes confromational change upon irradiation", J. American Chemical Soc., vol. 112, No. 13, pp. 5387-5388 (1990).
Zhang et al., "Structure, alternative splicing, and expression of the human RGS9 gene", Gene, vol. 240, No. 1, pp. 23-24 (1999).
Zhu et al., "A naturally occurring mutation of the opsin gene (T4R) in dogs affects glycosylation and stability of the G protein-coupled receptor", J. Biol. Chem., vol. 279, No. 51, pp. 53828-53839 (2004).
Haimovici et al., "Dark adaptation in age-related macu ar degeneration: relationship to the fellow eye", Graefe's Archive for Clinical and Experimental Ophthalmology, vol. 240, Iss. 2, pp, 90-95 (2002).
Jackson et al., "The Scotopic Sensitivity Tester-1 and the detection of early age-related macular degeneration", Ophthal. Physiol. Opt., vol. 26, No. 4, pp. 431-437 (2006).
Jackson et al., "A short-duration dark adaptation protocol for assessment of age-related maculopathy", J. Ocul. Biol. Dis. and Inf., vol. 1, Iss. 1, pp. 7-11 (2008).

\* cited by examiner

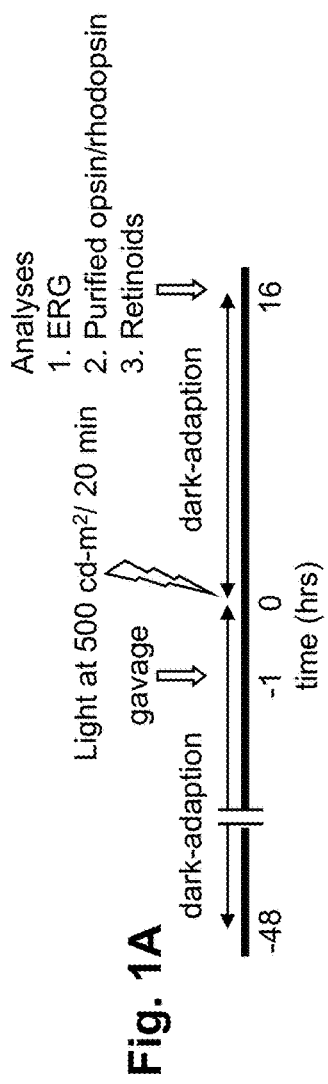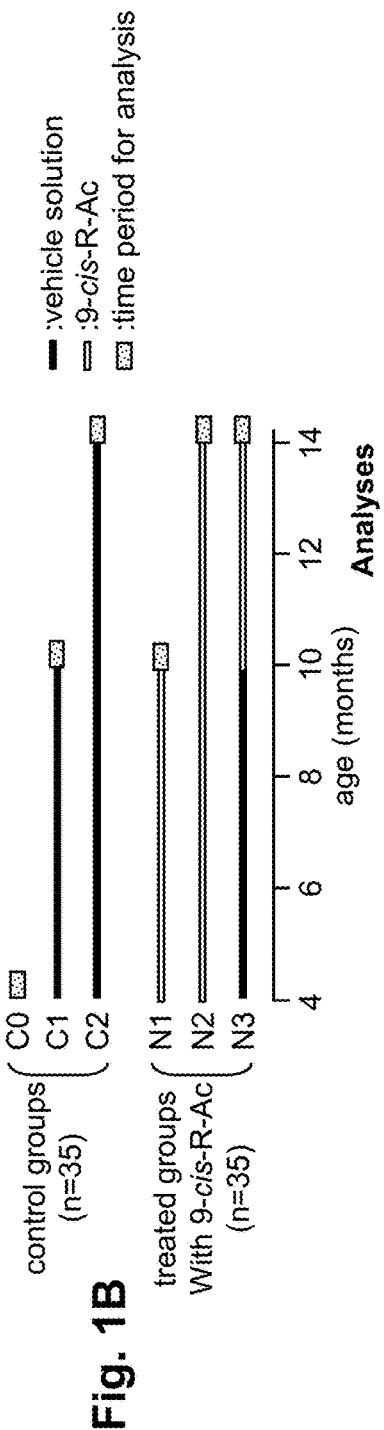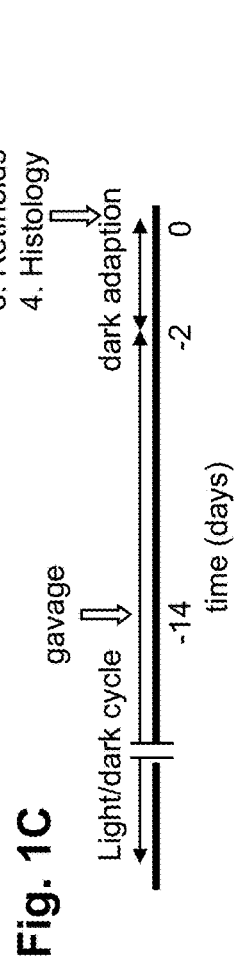

METHODS FOR THE TREATMENT AND PREVENTION OF AGE-RELATED RETINAL DYSFUNCTION

CROSS-REFERENCE TO RELATED APPLICATIONS

This application is a continuation of U.S. patent application Ser. No. 13/619,947, filed Sep. 14, 2012, now U.S. Pat. No. 9,408,821, which is a continuation of U.S. patent application Ser. No. 12/368,427, filed Feb. 10, 2009, now U.S. Pat. No. 8,324,270, which claims the benefit of priority to U.S. Provisional Patent Application No. 61/027,625, filed on Feb. 11, 2008, each of which is incorporated herein by reference in its entirety.

STATEMENT REGARDING GOVERNMENT INTEREST

This invention was made with government support under grants EY008061 and EY013385 awarded by the National Institutes of Health. The government has certain rights in the invention.

BACKGROUND

A diminished visual acuity or total loss of vision may result from a number of eye diseases or disorders caused by dysfunction of tissues or structures in the anterior segment of the eye and/or posterior segment of the eye. To understand why human vision declines with age, much research has focused on the retina, the layer of rod and cone photoreceptors cells that convert light into electrical signals. Studies in mice have shown that age-related decreases in retinal rod cell function cannot be explained by rod cell loss, abnormal retinal plasticity or any signs of retinal disease (Jackson, G. R., Owsley, C. & McGwin, G., Jr., Vision Research, 39, 3975-3982 (1999); Gao, H. & Hollyfield, J. G., Investigative Ophthalmology & Visual Science, 33, 1-17 (1992); Jackson, G. R., Owsley, C., Cordle, E. P. & Finley, C. D. Vision Research, 38, 3655-3662 (1998)). Indeed, Jackson and colleagues reported a dramatic slowing of rod-mediated dark adaptation after light exposure associated with human aging that was related to delayed regeneration of rhodopsin (Jackson, G. R., Owsley, C. & McGwin, G., Jr., Vision Research, 39, 3975-3982 (1999)).

Age related macular degeneration (AMD) is one of the specific diseases associated with the posterior portion of the eyeball and is the leading cause of blindness among older people. AMD results in damage to the macula, a small circular area in the center of the retina. Because the macula is the area which enables one to discern small details and to read or drive, its deterioration may bring about diminished visual acuity and even blindness. The retina contains two forms of light receiving cells, rods and cones, that change light into electrical signals. The brain then converts these signals into the images. The macula is rich in cone cells, which provides central vision. People with AMD suffer deterioration of central vision but usually retain peripheral sight.

Inadequate availability and/or processing of vitamin A to the visual chromophore, 11-cis-retinal, can adversely affect vertebrate rhodopsin regeneration and visual transduction (reviewed in McBee, J. K., Palczewski, K., Baehr, W. & Pepperberg, D. R., Prog Retin Eye Res, 20, 469-529 (2001); Lamb, T. D. & Pugh, E. N., Jr., Prog Retin Eye Res, 23, 307-380 (2004); and Travis, G. H., Golczak, M., Moise, A. R. & Palczewski, K., Annu Rev Pharmacol Toxicol (2006). As in aging, rhodopsin regeneration after light exposure is more delayed in humans and mice deprived of vitamin A due to either dietary deficiency or inadequate intestinal absorption (Lamb, T. D. & Pugh, E. N., Jr., Prog Retin Eye Res, 23, 307-380 (2004)). Moreover, treatment with vitamin A and its derivatives may have beneficial effects in aging (Jacobson, S. G., et al., Nat Genet, 11, 27-32 (1995)) and retinal diseases such as Sorbsby's fundus dystrophy (Jacobson, S. G., et al., Nat Genet, 11, 27-32 (1995)) and retinitis pigmentosa (Berson, E. L., et al., Arch Ophthalmol, 111, 761-772 (1993)).

Retinoid absorption, storage and recycling after bleaching of retinal pigments is impaired in mice lacking lecithin: retinol acyltransferase (LRAT) (Imanishi, Y., Batten, M. L., Piston, D. W., Baehr, W. & Palczewski, K., J Cell Biol 164, 373-383 (2004); Batten, M. L., et al., PLoS Medicine, 2, e333 (2005); Batten, M. L., et al., J Biol Chem, 279, 10422-10432 (2004); O'Byrne, S. M., et al., J Biol Chem, 280, 35647-35657 (2005)) and a null mutation in the human LRAT gene results in early-onset rod-cone dystrophy (Thompson, D. A., et al., Nat Genet, 28, 123-124 (2001)). The latter resembles a form of human Leber's congenital amaurosis (LCA) in which disabling mutations in the retinal pigment epithelium-specific 65 kDa (RPE65) gene also cause severe rod and cone photoreceptor dysfunction (Thompson, D. A., et al., Nat Genet, 28, 123-124 (2001)). LCA patients carrying mutations in both the LRAT and RPE65 genes may, like Lrat−/− and Rpe65−/− knockout mice, lack 11-cis-retinal and rhodopsin, possess abnormalities in all-trans-retinyl ester levels within RPE cells, show severe impairment of rod and cone photoreceptor functions and exhibit retinal degeneration (Imanishi, Y., Batten, M. L., Piston, D. W., Baehr, W. & Palczewski, K., J Cell Biol, 164, 373-383 (2004); Batten, M. L., et al. PLoS Medicine, 2, e333 (2005); Redmond, T. M., et al., Nat Genet, 20, 344-351 (1998); Van Hooser, J. P., et al., Proceedings of the National Academy of Sciences of the United States of America, 97, 8623-8628 (2000); Van Hooser, J. P., et al., J Biol Chem, 277, 19173-19182 (2002)).

The biochemical defects causing LCA-like symptoms in Lrat−/− and Rpe65−/− knockout mice can be bypassed by oral gavage with 9-cis-retinal. This treatment results in preserved retinal morphology and recovery of normal rod function as assessed by single cell recordings and ERG measurements (Batten, M. L., et al., PLoS Medicine, 2, e333 (2005); Van Hooser, J. P., et al., Proceedings of the National Academy of Sciences of the United States of America, 97, 8623-8628 (2000); Van Hooser, J. P., et al., J Biol Chem, 277, 19173-19182 (2002)). 9-cis-retinal forms photoactive isorhodopsin which, when bleached, undergoes conformational changes via the same photoproducts as does rhodopsin naturally regenerated from 11-cis-retinal (Yoshizawa, T. & Wald, G., Nature, 214, 566-571 (1967)). In addition, 11-cis-retinal given by intraperitoneal injection also improves vision in Rpe65−/− mice (Ablonczy, Z., et al., J Biol Chem, 277, 40491-40498 (2002)). Further, gastric gavage with a more chemically stable compound than either 9-cis- or 11-cis-retinal, i.e. 9-cis-retinyl acetate (9-cis-R-Ac), produces the same beneficial effects as 9-cis-retinal in Lrat−/− mice (Batten, M. L., et al., PLoS Medicine, 2, e333 (2005)). Other synthetic retinal derivatives that can be used to restore and/or stabilize photoreceptor function have been described, for example, in International Patent Publication No. WO 2006/002097 A2.

Currently, there are few treatments for retinoid deficiency. One treatment, a combination of antioxidant vitamins and zinc, produces only a small restorative effect by slowing the progression of AMD. Thus, there is a need for methods of restoring or stabilizing photoreceptor function in aging subjects. The present invention is related to the surprising discovery that long-term treatment with a synthetic retinoid derivative significantly improves age-related deterioration of photoreceptor function.

BRIEF SUMMARY

The present invention provides methods of treating or preventing age-related visual impairment comprising long-term administration of one or more synthetic retinal derivatives.

In one embodiment, the present invention provides a method of treating or preventing age-related retinal dysfunction in a subject comprising administering to the subject a pharmaceutically effective amount of a synthetic retinal derivative, wherein the synthetic retinal derivative is administered to the subject for a period of at least three months.

In one embodiment, the synthetic retinal derivative is administered to the subject about once every two weeks to about once every six weeks for a period of at least three months.

In another embodiment, the retinal derivative is administered to the subject about once a month for a period of from about 6 to about 10 months.

In another embodiment, the age-related retinal dysfunction is manifested by one or more of the following clinical conditions: an impairment in rod-mediated dark adaptation after light exposure, an impairment in night vision, an impairment in contrast sensitivity, and age-related macular degeneration (AMD).

In yet another embodiment, the present invention provides a method of improving rhodopsin regeneration ratio in a mammal comprising administering to the mammal a pharmaceutically effective amount of a synthetic retinal derivative, wherein the synthetic retinal derivative is administered to the mammal for a period of at least three months.

BRIEF DESCRIPTION OF THE DRAWINGS

FIGS. 1A, 1B, and 1C provide an experimental timeline for single dose treatment of 10-month-old mice with 9-cis-R-Ac and experimental protocols for long-term treatments. FIG. 1A: Fully dark-adapted (48 hr) 10-month-old mice were gavaged with 9-cis-R-Ac (~80 mg/kg body weight) or control vehicle solution. One hr after gavage, mice were exposed to continuous strong light at 500 cd·m$^{-2}$ for 20 min (~90% rhodopsin bleached) followed by 16 hr of dark adaptation. Mice then were examined by ERG, and analyzed for rhodopsin and retinoid content. ERGs also were recorded prior to the 9-cis-R-Ac treatment. Numbers of mice used for each analysis are shown in Table 1. FIG. 1B: Mice were gavaged with 9-cis-R-Ac (~80 mg/kg body weight) or vehicle solution (vegetable oil) once a month for 6 or 10 months as described in the Examples—Methods section. FIG. 1C: Group of mice were examined 2 weeks after the last gavage treatment either by ERG or for rhodopsin and retinoid content, and retinal morphology. Numbers of mice used for each analysis are shown in Table 1.

FIG. 3A: HPLC separation of retinoids from 9-cis-R-Ac treated and control mice. Fatty acid all-trans-retinyl esters eluted first (peak 1), followed by syn-11-cis-retinal oxime (2), syn-all-trans-retinal oxime (3), syn-9-cis-retinal oxime (4), and all-trans-retinol (5). Syn-retinal oximes are minor peaks on the chromatogram, and an asterisk (*) indicates a spike related to a solvent change. Inset(a), an expanded scale of the chromatogram shows peaks 3 and 4 corresponding to levels of syn-all-trans-retinal and syn-9-cis-retinal oximes. On-line spectra of these oximes are shown below (3 and 4). Retinoid levels in the eyes from treated and control mice (FIG. 1A) were analyzed by HPLC. Extraction procedures and derivatization with hydroxylamine to improve the recovery of retinals are described in the Examples—Methods section. FIGS. 3B and 3C: Quantification of retinals and esters. The amounts of 11-cis-retinal and all-trans-retinyl esters were similar in eyes of treated and control mice but 9-cis-retinal and 9-cis-retinyl esters were detected only in the eyes of 9-cis-R-Ac treated mice (n=3, P<0.0001). Levels of other non-polar retinoids were similar between 9-cis-R-Ac treated and untreated mice. A significant amount of 9-cis-retinal (peak 4) was detected in the sample from treated mice. Means±S.D. are indicated.

FIG. 4A: Scotopic and photopic ERG responses of 10-month-old mice. Responses of 9-cis-R-Ac treated mice were increased significantly under scotopic and photopic conditions (P<0.01) except for the a-wave amplitudes under photopic conditions (bottom left panel). FIG. 4B: Scotopic and photopic ERG responses of 14-month-old mice treated with 9-cis-R-Ac by two different regimes. No significant differences between treated and untreated groups of 14-month-old mice were observed under either scotopic or photopic conditions. Mice were dark-adapted for 48 hr prior to the ERGs (FIG. 1C). Scotopic (upper panels) and photopic (lower panels) ERGs were recorded as described in the Examples—Methods section. The a- and b-wave amplitudes were plotted as a function of light intensity. Error bars are indicated (n=10).

FIG. 5A: Recovery of 10-month-old mice from intense retinal bleaching. Different groups of 48 hr dark-adapted mice were bleached with intense constant illumination (500 cd·m$^{-2}$) for 3 min and a-wave amplitude recovery was monitored by recording single-flash ERGs (−0.2 log cd·s·m$^{-2}$) over the course of a 60 min dark adaptation period. The rate of recovery was significantly higher in treated mice (N1) than in the control mice (C1) at 10 months of age. Moreover, treatment with 9-cis-R-Ac restored the rate of recovery to that seen in 4-month-old mice. FIG. 5B: Recovery of 14-month-old mice from intense retinal bleaching. A significantly higher recovery rate occurred in treated (N2 and N3) versus untreated (C2) mice (*, n=5; P<0.01 and P<0.0001, respectively). Again, treated mice showed the same response as did young 4-month-old mice. Error bars are indicated (n=5).

FIG. 6A: Chromatographic separation and spectra of A2E and iso-A2E are shown. A representative HPLC chromatogram of eluted A2E and iso-A2E is shown from a group of N1 mice (left panel in A). Inset. Magnified elution areas of A2E and iso-A2E are highlighted. Spectra of these peaks (I and II) represent A2E and iso-A2E, respectively (top right). FIG. 6B: Amounts of A2E (black bars) and iso-A2E (grey bars) from different experimental groups are shown. Amounts of A2E did not differ significantly among all groups with the exception of N3, where they were slightly lower ($P<0.05$). Iso-A2E levels were similar among all groups. Neither compound was detected at significant levels in young untreated mice (C0). Means±S.D. are indicated.

DETAILED DESCRIPTION

Figure 2:
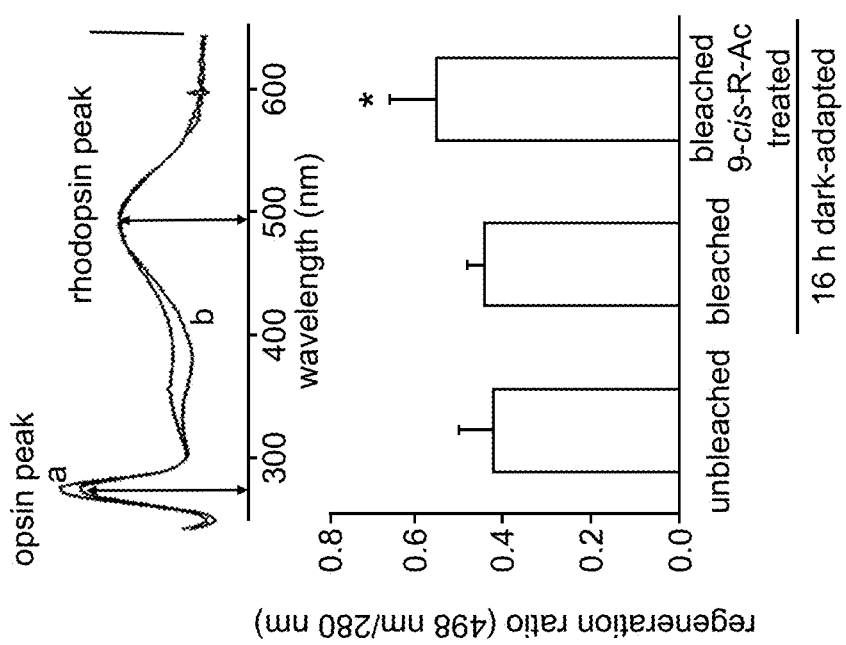
FIG. 2 shows the characterization of purified rhodopsin/opsin from 9-cis-R-Ac treated and control mice. Co-eluted rhodopsin and opsin were purified as described in the Examples—Methods section from mice treated as described in FIG. 1. The regeneration level of rhodopsin was calculated from the ratio of absorbance at 498 nm (opsin with the chromophore)/280 nm (total opsin). Above. Representative absorbance spectra of purified rhodopsin from 10-month-old 9-cis-R-Ac treated mouse (a) and control mouse (b) are shown. The bar indicates 0.02 AU. Below. The regeneration ratio of the 9-cis-R-Ac treated group was slightly higher than the control group, indicating the treated group had a lower level of unliganded (free) opsin (a). Means±S.D. are indicated.

The present methods are directed to treating or preventing age-related retinal dysfunction in a subject via long-term administration of a pharmaceutically effective amount of a synthetic retinal derivative.

As used herein, the term "age-related retinal dysfunction" refers to age-related decreases in retinal photoreceptor function. The term is meant to include the age-related impairments related to electroretinogram deficits and photoreceptor cell death and structural abnormalities that have been observed in both animal and human studies of aging. In one aspect, the age-related retinal dysfunction comprises a slowing of rod-mediated dark adaptation after light exposure, a decrease in night vision, and/or a decrease in contrast sensitivity. In another aspect, the age-related retinal dysfunction comprises age-related macular degeneration (AMD). The AMD can be wet or dry forms.

The terms "treating," treatment," and the like are used herein to generally mean obtaining a desired pharmacological and physiological effect. More specifically, the synthetic retinal derivatives described herein which are used to treat a subject with age-related retinal dysfunction generally are provided in a therapeutically effective amount to achieve an improvement in age-related retinal dysfunction or an inhibited development of age-related retinal dysfunction in the visual system of an ageing subject, as compared with a comparable visual system not receiving the synthetic retinal derivative. An improvement in age-related retinal dysfunction includes long-term (e.g., as measured in weeks or months) improvement or restoration of photoreceptor function in a visual system, as compared with a comparable visual system not receiving the synthetic retinal derivative. Improvement also includes stabilization of, or minimization of additional degradation in, a vertebrate visual system, as compared with a comparable vertebrate visual system not receiving the synthetic retinal derivative.

The terms "preventing," "prevention," and the like are used generally to mean preventing or inhibiting deterioration or further deterioration of the visual system of an aging subject, as compared with a comparable visual system not receiving the synthetic retinal derivative.

The term "pharmaceutically effective" as used herein refers to the effectiveness of a particular treatment or prevention regime. Pharmaceutical efficacy can be measured based on such characteristics as, for example, an increased or stabilized rate of dark-adaptation, a higher or stabilized rhodpsin/opsin ratio, a higher or stabilized rhodopsin regeneration rate, or other such improvements in electrotretinographic (ERG) responses.

In the present methods, a synthetic retinal derivative is administered to a subject. As used herein, the term "subject" or "patient" refers to a vertebrate, for example a mammal such as a human. In one embodiment, the subject is an aging subject, such as a human, suffering from age-related retinal dysfunction. As used herein, an aging human subject is typically at least 45, or at least 50, or at least 60, or at least 65 years old. The subject has an aging eye, which is characterized as having age-related retinal dysfunction. Age-related retinal dysfunction may be manifested by one or more of the following clinical conditions: an impairment in rod-mediated dark adaptation after light exposure, an impairment in night vision, an impairment in contrast sensitivity, and age-related macular degeneration (AMD).

The synthetic retinal derivative is administered using long-term (chronic) dosage regimens. In one embodiment, the synthetic retinal derivative is administered intermittently for three months or longer; and, in another embodiment, for six months or longer. The synthetic retinal derivative can be administered, for example, for a period of about three, four, five, six, seven, eight, nine, ten, eleven, or twelve months, or longer. The synthetic retinal derivative can be intermittently administered to the subject about once a day to about once every two months. Intermittent administration includes administration to the subject about once every other day; about four times a week, three times a week, and two times a week; about once every two, three, four, five, six, seven, eight, and nine weeks; and about once a month. In one embodiment, the synthetic retinal derivative is administered about once every three to six weeks for a period of about three months or longer; and in another embodiment, it is administered about once a month for about six to ten months.

The amount of synthetic retinal derivative administered per dose can be increased as the time period between doses is increased. For example, if the synthetic retinal derivative is administered less than once a day, the dose per administration can be greater than the effective daily dose. As used herein, an "effective daily dose" refers to a daily dose effective for obtaining a desired pharmacological and physiological effect (i.e. a daily dose effective for "treating" and/or "preventing" age related retinal dysfunction in a subject as described above).

In addition, the synthetic retinal derivative can be chronically released from a controlled drug delivery formulation and/or device for an extended period of time, e.g., for a period of about three months or longer; or for a period of about six months or longer. A wide variety of methods for controlled release have been developed and are known to those skilled in the art, including pumps, patches, tablets, implants, microchips, and polymeric systems.

Suitable doses of synthetic retinal derivatives will depend on the clinical status, condition and age of the patient, the active agent, the formulation and dosage form, the frequency of dosing, and the like. In many instances the selection of an appropriate dose will be within the skill of a suitable healthcare practitioner such as a physician or nurse. In the case of eye drops, a synthetic retinal derivative can be administered, for example, from about 0.01 mg, about 0.1 mg, or about 1 mg, to about 25 mg, to about 50 mg, or to about 90 mg per single dose. In the case of injection, suitable doses are about 0.0001 mg, about 0.001 mg, about 0.01 mg, or about 0.1 mg to about 10 mg, to about 25 mg, to about 50 mg, or to about 500 mg of the synthetic retinal derivative. Suitable oral doses range from about 0.1 to about 1000 mg of the synthetic retinal derivative. In other embodiments, about 1.0 to about 300 mg of synthetic retinal derivative can be administered per dose.

In certain embodiments, the dose is an oral dose of about 0.01 to about 10 mg/kg body weight; about 0.05 to about 7.5 mg/kg body weight; about 0.1 to about 5 mg/kg body weight; or about 0.5 to about 2.5 mg/kg body weight. For example, the synthetic retinal derivative can be administered at an oral dosage of about 6.4 mg/kg body weight (i.e. about 240 mg/m² body surface area). In another embodiment, the dose is an oral daily dose of about 0.1 to about 1 mg/kg body weight, such as an oral daily dose of about 0.1, 0.2, 0.3, 0.4, 0.5, 0.6, 0.7, 0.8, 0.9, or 1 mg/kg body weight.

Synthetic retinal derivatives suitable for the methods of the present invention have been described in International Patent Publication Nos. WO 2004/082622 A2, published in the U.S. as US 2004/0242704, and WO 2006/002097 A2, published in the U.S. as US 2008/0221208 and in U.S. Patent Publication No. 2004/0242704A1.

A synthetic retinal derivative suitable for the methods of the present invention is a derivative of 9-cis-retinal or 11-cis-retinal in which the aldehydic group in the polyene chain is modified. The synthetic retinal derivative can be converted directly or indirectly into a retinal or a synthetic retinal analog. Thus, in some aspects, the compounds according to the present invention can be described as pro-drugs, which upon metabolic transformation are converted into 9-cis-retinal, 11-cis-retinal or a synthetic retinal analog thereof. Metabolic transformation can occur, for example, by acid hydrolysis, esterase activity, acetyltransferase activity, dehydrogenase activity, or the like.

The synthetic retinal derivative can be a retinoid replacement, supplementing the levels of endogenous retinoid. In some embodiments, the synthetic retinal can bind to opsin, and function as an opsin agonist. As used herein, the term "agonist" refers to a synthetic retinal that binds to opsin and facilitates the ability of an opsin/synthetic retinal complex to respond to light. As an opsin agonist, a synthetic retinal can spare the requirement for endogenous retinoid (e.g., 11-cis-retinal). A synthetic retinal also can restore or improve function (e.g., photoreception) to opsin by binding to opsin and forming a functional opsin/synthetic retinal complex, whereby the opsin/synthetic retinal complex can respond to photons when part of a rod or cone membrane.

Synthetic retinal derivatives can be administered to restore or stabilize photoreceptor function, and/or to ameliorate the effects of a deficiency in retinoid levels. Photoreceptor function can be restored or stabilized, for example, by providing a synthetic retinal derivative as an 11-cis-retinoid replacement and/or an opsin agonist. The synthetic retinal derivative also can ameliorate the effects of a retinoid deficiency on a vertebrate visual system. The synthetic retinal derivative can be administered prophylactically or therapeutically to a vertebrate. Suitable vertebrates include, for example, human and non-human vertebrates. Suitable non-human vertebrates include, for example, mammals, such as dogs (canine), cats (feline), horses (equine) and other domesticated animals.

In one aspect of the invention, the synthetic retinal derivatives are derivatives of 9-cis-retinal or 11-cis-retinal in which the aldehydic group in the polyene chain is converted to an ester, ether, alcohol, hemi-acetal, acetal, or oxime, as further described herein. Such synthetic retinal derivatives include 9-cis-retinyl esters, 9-cis-retinyl ethers, 9-cis-retinol, 9-cis retinyl oximes, 9-cis-retinyl acetals, 9-cis-retinyl hemiacetals, 11-cis-retinyl esters, 11-cis-retinyl ethers, 11-cis-retinol, 11-cis-retinyl oximes, 11-cis-retinyl acetals and II-cis-retinyl hemiacetals, as further described herein. The synthetic retinal derivative can be metabolized to release a natural or synthetic retinal, such as for example, 9-cis-retinal, 11-cis-retinal or a synthetic retinal analog thereof, such as those described herein or in International Patent Publication Nos. WO 2004/082622 A2, published in the U.S. as US 2004/0242704, and WO 2006/002097 A2, published in the U.S. as US 2008/0221208.

In one aspect, the synthetic retinal derivative is a retinyl ester. In some embodiments, the retinyl ester is a 9-cis-retinyl ester or an 11-cis-retinyl ester having a. The ester substituent can be, for example, a carboxylic acid, such as a mono- or polycarboxylic acid. As used herein, a "polycarboxylic acid" is a di-, tri- or higher order carboxylic acid. In some embodiments, the carboxylic acid is a $C_1$-$C_{22}$, $C_2$-$C_{22}$, $C_3$-$C_{22}$, $C_1$-$C_{10}$, $C_2$-$C_{10}$, $C_3$-$C_{10}$, $C_4$-$C_{10}$, $C_4$-$C_8$, $C_4$-$C_6$ or $C_4$ monocarboxylic acid, or polycarboxylic acid.

Suitable carboxylic acid groups include, for example, acetic acid, propionic acid, butyric acid, valeric acid, caproic acid, caprylic acid, pelargonic acid, capric acid, lauric acid, oleic acid, stearic acid, palmitic acid, myristic acid or linoleic acid. The carboxylic acid also can be, for example, oxalic acid (ethanedioic acid), malonic acid (propanedioic acid), succinic acid (butanedioic), fumaric acid (butenedioic acid), malic acid (2-hydroxybutenedioic acid), glutaric acid (pentanedioic acid), adipic acid (hexanedioic acid), pimelic acid (heptanedioic), suberic acid (octanedioic), azelaic acid (nonanedioic acid), sebacic acid (decanedioic acid), citric acid, oxaloacetic acid, ketoglutaratic acid, or the like.

In an exemplary embodiment, the retinyl ester is a 9-cis-retinyl ester or an 11-cis-retinyl ester including a $C_3$-$C_{10}$ polycarboxylic acid substituent. (In this context, the terms "substituent" or "group" refer to a radical covalently linked to the terminal oxygen in the polyene chain.) In another exemplary embodiment, the retinyl ester is a 9-cis-retinyl ester or an 11-cis-retinyl ester including a $C_2$-$C_{22}$ or $C_3$-$C_{22}$ polycarboxylic acid substituent. The polycarboxylic acid substituent can be, for example, succinate, citrate, ketoglutarate, fumarate, malate or oxaloacetate. In another exemplary embodiment, the retinyl ester is a 9-cis-retinyl ester or an 11-cis-retinyl ester including a $C_3$-$C_{22}$ di-carboxylic acid (di-acid) substituent. In some embodiments, the polycarboxylic acid is not 9-cis-retinyl tartarate or 11-cis-retinyl tartarate. In some embodiments, the retinyl ester is not a naturally occurring retinyl ester normally found in the eye. In some embodiments, the retinyl ester is an isolated retinyl ester. As used herein, "isolated" refers to a molecule that exists apart from its native environment and is therefore not a product of nature. An isolated molecule may exist in a purified form or may exist in a non-native environment.

In another aspect, the retinal derivative can be a 9-cis-retinyl ester or ether of the following formula I:

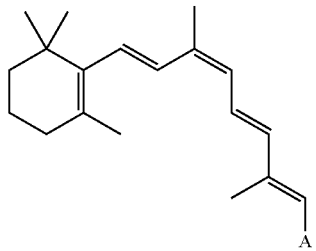

(I)

In some embodiments, A is $CH_2OR$, where R can be an aldehydic group, to form a retinyl ester. A suitable aldehydic group is a $C_1$ to $C_{24}$ straight chain or branched aldehydic group. The aldehydic group also can be a $C_1$ to $C_{14}$ straight chain or branched aldehydic group. The aldehydic group can be a $C_1$ to $C_{12}$ straight chain or branched aldehydic group, such as, for example, acetaldehyde, propionaldehyde, butyraldehyde, valeraldehyde, hexanal, heptanal, octanal, nonanal, decanal, undecanal, dodecanal. R can be a $C_1$ to $C_{10}$ straight chain or branched aldehydic group, a $C_1$ to $C_8$ straight chain or branched aldehydic group or a $C_1$ to $C_6$ straight chain or branched aldehydic group.

R further can be a carboxylate group of a dicarboxylic acid or other carboxylic acid (e.g., a hydroxyl acid) to form a retinyl ester (some of which are also referred to as retinoyl esters). The carboxylic acid can be, for example, oxalic acid (ethanedioic acid), malonic acid (propanedioic acid), succinic acid (butanedioic), fumaric acid (butenedioic acid), malic acid (2-hydroxybutenedioic acid), glutaric acid (pentanedioic acid), adipic acid (hexanedioic acid), pimelic acid (heptanedioic), suberic acid (octanedioic), azelaic acid (nonanedioic acid), sebacic acid (decanedioic acid), citric acid, oxaloacetic acid, ketoglutaratic acid, or the like.

R can also be an alkane group, to form a retinyl alkane ether. Suitable alkane groups include, for example, $C_1$ to $C_{24}$ straight chain or branched alkyls, such as, for example, methane, ethane, butane, isobutane, pentane, isopentane, hexane, heptane, octane or the like. For example, the alkane group can be a linear, iso-, sec-, tert- or other branched lower alkyl ranging from $C_1$ to $C_6$. The alkane group also can be a linear, iso-, sec-, tert- or other branched medium chain length alkyl ranging from $C_8$ to $C_{14}$. The alkane group also can be a linear, iso-, sec-, tert- or other branched long chain length alkyl ranging from $C_{16}$ to $C_{24}$.

R further can be an alcohol group, to form a retinyl alcohol ether. Suitable alcohol groups can be linear, iso-, sec-, tert- or other branched lower alcohols ranging from $C_1$ to $C_6$, linear, iso-, sec-, tert- or other branched medium chain length alcohols ranging from $C_8$ to $C_{14}$, or linear, iso-, sec-, tert- or other branched long chain length alkyl ranging from $C_{16}$ to $C_{24}$. The alcohol group can be, for example, methanol, ethanol, butanol, isobutanol, pentanol, hexanol, heptanol, octanol, or the like R also can be a carboxylic acid, to form a retinyl carboxylic acid ether. Suitable alcohol groups can be linear, iso-, sec-, ted- or other branched lower carboxylic acids ranging from $C_1$ to $C_6$, linear, iso-, sec-, ted- or other branched medium chain length carboxylic acids ranging from $C_8$ to $C_{14}$, or linear, iso-, sec-, tert- or other branched long chain length carboxylic acids ranging from $C_{16}$ to $C_{24}$. Suitable carboxylic acid groups include, for example, acetic acid, propionic acid, butyric acid, valeric acid, caproic acid, caprylic acid, pelargonic acid, capric acid, lauric acid, oleic acid, stearic acid, palmitic acid, myristic acid, linoleic acid, succinic acid, fumaric acid or the like.

The retinyl derivative can be a retinyl hemiacetal, where A is CH(OH)OR. R can be any of the R groups set forth above in Formula I. R is typically a lower alkane, such as a methyl or ethyl group, or a $C_1$ to $C_7$ saturated and unsaturated, cyclic or acyclic alkane, with or without hetero atoms, as described herein.

The retinyl derivative can be a retinyl acetal, where A is CH $(OR_a)OR_b$. Each of $R_a$ and $R_b$ can be independently selected from any of the R groups set forth above in Formula I. $R_a$ and $R_b$ are typically a $C_1$ to $C_7$ saturated and unsaturated, cyclic or acyclic alkane, with or without hetero atoms, as described herein.

The retinyl derivative also can be a retinyl oxime, where A is CH:NOH or CH:NOR. R can be any of the R groups set forth above in Formula I. R is typically a hydrogen, or an alkane.

Examples of suitable synthetic retinal derivatives include, for example, 9-cis-retinyl acetate, 9-cis-retinyl formate, 9-cis-retinyl succinate, 9-cis-retinyl citrate, 9-cis-retinyl ketoglutarate, 9-cis-retinyl fumarate, 9-cis-retinyl malate, 9-cis-retinyl oxaloacetate, 9-cis-retinal oxime, 9-cis-retinal O-methyl oximes, 9-cis-retinal O-ethyl oximes, and 9-cis-retinal methyl acetals and hemi acetals, 9-cis-retinyl methyl ether, 9-cis-retinyl ethyl ether, and 9-cis-retinyl phenyl ether.

In a related aspect, the retinal derivative can be an 11-cis-retinyl ester or ether of the following formula II:

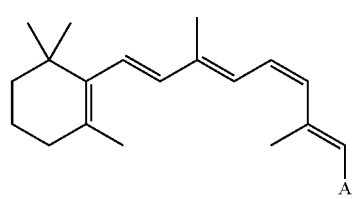

(II)

A can be any of the groups set forth above in Formula I.

Examples of suitable synthetic retinal derivatives include, for example, 11-cis-retinyl acetate, 11-cis-retinyl formate, 11-cis-retinyl succinate, 11-cis-retinyl citrate, 11-cis-retinyl ketoglutarate, 11-cis-retinyl fumarate, 11-cis-retinyl malate, 11-cis-retinal oxime, 11-cis-retinal O-methyl oxime, 11-cis-retinal O-ethyl oximes and 11-cis-retinal methyl acetals and hemi acetals, 11-cis-retinyl methyl ether, 11-cis-retinyl ethyl ether.

In additional aspects, the synthetic retinal derivatives can be, for example, a derivative of a 9-cis-retinyl ester, a 9-cis-retinyl ether, an 11-cis-retinyl ester or an 11-cis-retinyl ethers such as, for example, an acyclic retinyl ester or ethers, a retinyl ester or ether with a modified polyene chain length, such as a trienoic or tetraenoic retinyl ester or ether; a retinyl ester or ether with a substituted polyene chain, such as alkyl, halogen or heteratom-substituted polyene chains; a retinyl ester or ether with a modified polyene chain, such as a trans- or cis-locked polyene chain, or with, for example, allene or alkyne modifications; and a retinyl ester or ether with a ring modification(s), such as heterocyclic, heteroaromatic or substituted cycloalkane or cycloalkene rings.

The synthetic retinal derivative can be a retinyl ester or ether of the following formula III:

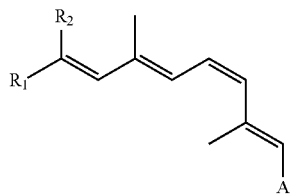

A can be any of the groups set forth above for formula (I). $R_1$ and $R_2$ can be independently selected from linear, iso-, sec-, tert- and other branched alkyl groups as well as substituted alkyl groups, substituted branched alkyl, hydroxyl, hydroalkyl, amine, amide, or the like. $R_1$ and $R_2$ can independently be lower alkyl, which means straight or branched alkyl with 1-6 carbon atom(s) such as methyl, ethyl, propyl, isopropyl, butyl, isobutyl, tert-butyl, pentyl, hexyl, or the like. Suitable substituted alkyls and substituted branch alkyls include, for example, alkyls, branched alkyls and cyclo-alkyls substituted with oxygen, hydroxyl, nitrogen, amide, amine, halogen, heteroatom or other groups. Suitable heteroatoms include, for example, sulfur, silicon, and fluoro- or bromo-substitutions.

$R_1$ or $R_2$ also can be a cyclo-alkyl such as, for example, hexane, cyclohexene, benzene as well as a substituted cyclo-alkyl. Suitable substituted cyclo-alkyls include, for example, cyclo-alkyls substituted with oxygen, hydroxyl, nitrogen, amide, amine, halogen, heteroatom and/or other groups. Suitable heteroatoms include, for example, sulfur, silicon, and fluoro- or bromo-substitutions.

The synthetic retinal derivative also can have a modified polyene chain length, such as the following formula IV:

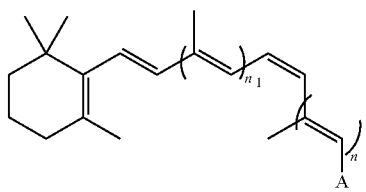

A can be any of the groups set forth above for formula (I). The polyene chain length can be extended by 1, 2, or 3 alkyl, alkene or alkylene groups. According to formula (IV), each n and $n_1$ can be independently selected from 1, 2, or 3 alkyl, alkene or alkylene groups, with the proviso that the sum of the n and $n_1$ is at least 1.

The synthetic retinal derivative also can have a substituted polyene chain of the following formula V:

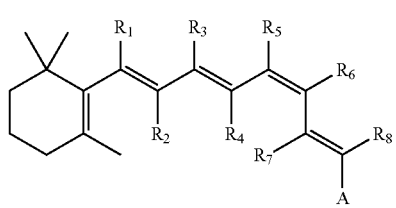

A can be any of the groups set forth above for formula (I). Each of $R_1$ to $R_8$ can be independently selected from hydrogen, alkyl, branched alkyl, cyclo-alkyl, halogen, a heteratom, or the like. Suitable alkyls include, for example, methyl, ethyl, propyl, substituted alkyl (e.g., alkyl with hydroxyl, hydroalkyl, amine, amide) or the like. Suitable branched alkyls can be, for example, isopropyl, isobutyl, substituted branched alkyl, or the like. Suitable cyclo-alkyls can include, for example, cyclohexane, cycloheptane, and other cyclic alkanes as well as substituted cyclic alkanes such as substituted cyclohexane or substituted cycloheptane. Suitable halogens include, for example, bromine, chlorine, fluorine, or the like. Suitable heteroatoms include, for example, sulfur, silicon, and fluoro- or bromo-substitutions. Suitable substituted alkyls, substituted branch alkyls and substituted cyclo-alkyls include, for example, alkyls, branched alkyls and cyclo-alkyls substituted with oxygen, hydroxyl, nitrogen, amide, amine, halogen, heteroatom or other groups.

For example, the synthetic retinal derivative can be selected from the following: a 9-ethyl-11-cis-retinyl ester, ether, oxime, acetal or hemiacetal; a 7-methyl-11-cis-retinyl ester, ether, oxime, acetal or hemiacetal; a 13-desmethyl-11-cis-retinyl ester, ether, oxime, acetal or hemiacetal; an 11-cis-10-F-retinyl ester, ether, oxime, acetal or hemiacetal; an 11-cis-10-Cl-retinyl ester, ether, oxime, acetal or hemiacetal; an 11-cis-10-methyl-retinyl ester, ether, oxime, acetal or hemiacetal; an 11-cis-10-ethyl-retinyl ester, ether, oxime, acetal or hemiacetal; a 9-cis-10-F-retinyl ester, ether, oxime, acetal or hemiacetal; a 9-cis-10-Cl-retinyl ester, ether, oxime, acetal or hemiacetal; a 9-cis-10-methyl-retinyl ester, ether, oxime, acetal or hemiacetal; a 9-cis-10-ethyl-retinyl ester, ether, oxime, acetal or hemiacetal; an 11-cis-12-F-retinyl ester, ether, oxime, acetal or hemiacetal; an 11-cis-12-Cl-retinyl ester, ether, oxime, acetal or hemiacetal; an 11-cis-12-methyl-retinyl ester, ether, oxime, acetal or hemiacetal; an 11-cis-10-ethyl-retinyl ester, ether, oxime, acetal or hemiacetal; a 9-cis-12-F-retinyl ester, ether, oxime, acetal or hemiacetal; a 9-cis-12-Cl-retinyl ester, ether, oxime, acetal or hemiacetal; a 9-cis-12-methyl-retinyl ester, ether, oxime, acetal or hemiacetal; an 11-cis-14-F-retinyl ester, ether, oxime, acetal or hemiacetal; an 11-cis-14-methyl-retinyl ester, ether, oxime, acetal or hemiacetal; an 11-cis-14-ethyl-retinyl ester, ether, oxime, acetal or hemiacetal; a 9-cis-14-F-retinyl ester, ether, oxime, acetal or hemiacetal; a 9-cis-14-methyl-retinyl ester, ether, oxime, acetal or hemiacetal; a 9-cis-14-ethyl-retinyl ester, ether, oxime, acetal or hemiacetal; or the like.

The synthetic retinal derivative further can have a modified ring structure. Suitable examples include, for example, derivatives containing ring modifications, aromatic analogs and heteroaromatic analogs of the following formulae VI, VII and VIII, respectively:

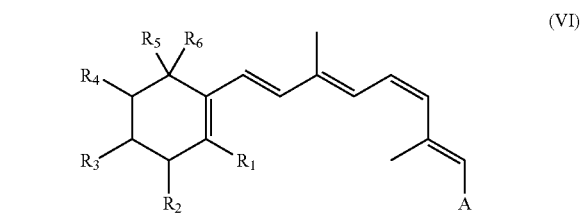

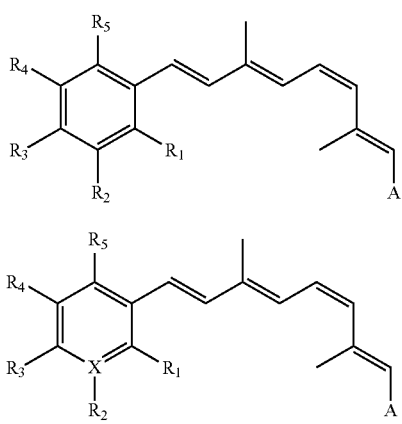

(VII)

(VIII)

A can be any of the groups set forth above for formula (I). Each of $R_1$ to $R_6$, as applicable, can be independently selected from hydrogen, alkyl, substituted alkyl, hydroxyl, hydroalkyl, amine, amide, halogen, a heteratom, or the like. Suitable alkyls include, for example, methyl, ethyl, propyl, isopropyl, butyl, isobutyl or the like. Suitable halogens include, for example, bromine, chlorine, fluorine, or the like. Suitable heteroatoms include, for example, sulfur, silicon, or nitrogen. In formulae VII, X can be, for example, sulfur, silicon, nitrogen, fluoro- or bromo-substitutions. Similarly, 9-cis-synthetic retinal derivatives containing ring modifications, aromatic analogs and heteroaromatic analogs of those shown in formulae VI, VII and VIII are contemplated.

The synthetic retinal derivative also can have a modified polyene chain. Suitable derivatives include, for example, those with a trans/cis locked configuration, 6s-locked analogs, as well as modified allene, alkene, alkyne or alkylene groups in the polyene chain. In one example, the derivative is an 11-cis-locked analog of the following formula IX:

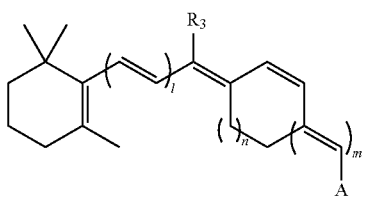

(IX)

A can be any of the groups set forth above for formula (I). $R_3$ can be, for example, hydrogen, methyl or other lower alkane or branch alkane. n can be 0 to 4. m plus 1 equals 1, 2 or 3.

In one embodiment, the synthetic retinal derivative can be an 11-cis-locked analog of the following formula X:

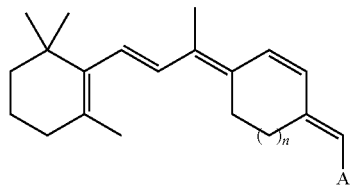

(X)

n can be 1 to 4. A can be any of the groups set forth above for formula (I).

The synthetic retinal derivative is a 9,11,13-tri-cis-7-ring retinyl ester or ether, an 11,13-di-cis-7-ring retinyl ester or ether, an 11-cis-7-ring retinyl ester or ether or a 9,11-di-cis-7-ring retinyl ester or ether.

In another example, the synthetic retinal derivative is a 6s-locked analog of formula XI. A can be any of the groups set forth above for formula (I). $R_1$ and $R_2$ can be independently selected from hydrogen, methyl and other lower alkyl and substituted lower alkyl. $R_3$ can be independently selected from an alkene group at either of the indicated positions.

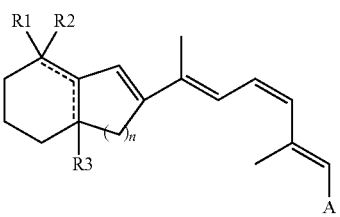

(XI)

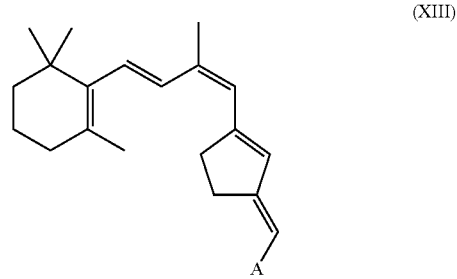

(XII)

(XIII)

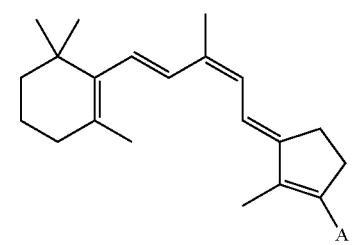

(XIV)

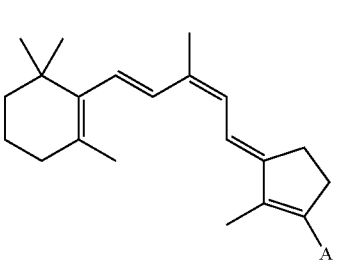

The synthetic retinal derivative can be a 9-cis-ring-fused derivative, such as, for example, those shown in formulae XII-XIV. A can be any of the groups set forth above for formula (I).

The synthetic retinal derivative also can be of the following formula XV or XVI.

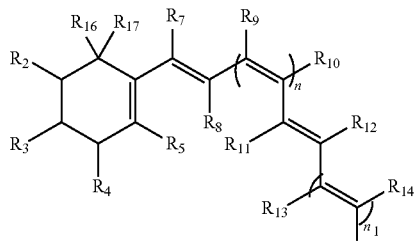

(XV)

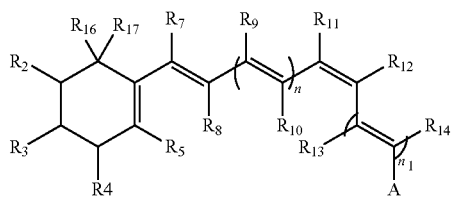

(XVI)

A can be any of the groups set forth above for formula (I). Each of $R_2$ to $R_5$, $R_7$ to $R_{14}$, $R_{16}$ and $R_{17}$ can be absent or independently selected from hydrogen, alkyl, branched alkyl, halogen, hydroxyl, hydroalkyl, amine, amide, a heteratom, or the like. Suitable alkyls include, for example, methyl, ethyl, propyl, substituted alkyl (e.g., alkyl with hydroxyl, hydroalkyl, amine, amide), or the like. Suitable branched alkyl can be, for example, isopropyl, isobutyl, substituted branched alkyl, or the like. Suitable halogens include, for example, bromine, chlorine, fluorine, or the like. Suitable heteroatoms include, for example, sulfur, silicon, and fluoro- or bromo-substitutions. Suitable substituted alkyls and substituted branch alkyls include, for example, alkyls and branched alkyls substituted with oxygen, hydroxyl, nitrogen, amide, amine, halogen, heteroatom or other groups. Each of n and $n_1$ can be independently selected from 1, 2, or 3 alkyl, alkene or alkylene groups, with the proviso that the sum of the n and $n_1$ is at least 1. In addition, $R_3$-$R_4$ and/or $R_2$-$R_{16}$ can comprise an alkene group in the cyclic carbon ring, in which case $R_{17}$ is absent. $R_{10}$ and $R_{13}$ together can form a cyclo-alkyl, such as a five, six, seven or eight member cyclo-alkyl or substituted cyclo-alkyl, such as, for example, those shown in Formulae IX, X, XII, XIII and XIV.

Methods of making synthetic retinals and derivatives are disclosed in, for example, the following references: *Anal. Biochem.* 272:232-42 (1999); *Angew. Chem.* 36:2089-93 (1997); *Biochemistry* 14:3933-41 (1975); *Biochemistry* 21:384-93 (1982); *Biochemistry* 28:2732-39 (1989); *Biochemistry* 33:408-16 (1994); *Biochemistry* 35:6257-62 (1996); *Bioorganic Chemistry* 27:372-82 (1999); *Biophys. Chem.* 56:31-39 (1995); *Biophys. J.* 56:1259-65 (1989); *Biophys. J.* 83:3460-69 (2002); *Chemistry* 7:4198-204 (2001); *Chemistry* (Europe) 5:1172-75 (1999); *FEBS* 158:1 (1983); *J. Am. Chem. Soc.* 104:3214-16 (1982); *J. Am. Chem. Soc.* 108:6077-78 (1986); *J. Am. Chem. Soc.* 109: 6163 (1987); *J. Am. Chem. Soc.* 112:7779-82 (1990); *J. Am. Chem. Soc.* 119:5758-59 (1997); *J. Am. Chem. Soc.* 121: 5803-04 (1999); *J. American Chem. Soc.* 123:10024-29 (2001); *J. American Chem. Soc.* 124:7294-302 (2002); *J. Biol. Chem.* 276:26148-53 (2001); *J. Biol. Chem.* 277: 42315-24 (2004); *J. Chem. Soc.-Perkin T.* 1:1773-77 (1997); *J. Chem. Soc-Perkin T.* 1:2430-39 (2001); *J. Org. Chem.* 49:649-52 (1984); *J. Org. Chem.* 58:3533-37 (1993); *J. Physical Chemistry B* 102:2787-806 (1998); *Lipids* 8:558-65; *Photochem. Photobiol.* 13:259-83 (1986); *Photochem. Photobiol.* 44:803-07 (1986); *Photochem. Photobiol.* 54:969-76 (1991); *Photochem. Photobiol.* 60:64-68 (1994); *Photochem. Photobiol.* 65:1047-55 (1991); *Photochem. Photobiol.* 70:111-15 (2002); *Photochem. Photobiol.* 76:606-615 (2002); *Proc. Natl Acad. Sci. USA* 88:9412-16 (1991); *Proc. Natl Acad. Sci. USA* 90:4072-76 (1993); *Proc. Natl Acad. Sci. USA* 94:13442-47 (1997); and *Proc. R. Soc. Lond. Series B, Biol. Sci.* 233(1270): 55-76 1988) (the disclosures of which are incorporated by reference herein).

Retinyl esters can be formed by methods known in the art such as, for example, by acid-catalyzed esterification of a retinol with a carboxylic acid, by reaction of an acyl halide with a retinol, by transesterification of a retinyl ester with a carboxylic acid, by reaction of a primary halide with a carboxylate salt of a retinoic acid, by acid-catalyzed reaction of an anhydride with a retinol, or the like. In an example, retinyl esters can be formed by acid-catalyzed esterification of a retinol with a carboxylic acid, such as, acetic acid, propionic acid, butyric acid, valeric acid, caproic acid, caprylic acid, pelargonic acid, capric acid, lauric acid, oleic acid, stearatic acid, palmitic acid, myristic acid, linoleic acid, succinic acid, fumaric acid or the like. In another example, retinyl esters can be formed by reaction of an acyl halide with a retinol (see, e.g., Van Hooser et al., *Proc. Natl. Acad. Sci., USA,* 97:8623-28 (2000)). Suitable acyl halides include, for example, acetyl chloride, palmitoyl chloride, or the like.

Retinyl ethers can be formed by methods known in the art, such as for example, reaction of a retinol with a primary alkyl halide.

Trans-retinoids can be isomerized to cis-retinoids by exposure to UV light. For example, all-trans-retinal, all-trans-retinol, all-trans-retinyl ester or all-trans-retinoic acid can be isomerized to 9-cis-retinal, 9-cis-retinol, 9-cis-retinyl ester or 9-cis-retinoic acid, respectively. trans-Retinoids can be isomerized to 9-cis-retinoids by, for example, exposure to a UV light having a wavelength of about 365 nm, and substantially free of shorter wavelengths that cause degradation of cis-retinoids, as further described herein.

Retinyl acetals and hemiacetals can be prepared, for example, by treatment of 9-cis- and 11-cis-retinals with alcohols in the presence of acid catalysts. Water formed during reaction is removed, for example by $Al_2O_3$ of a molecular sieve.

Retinyl oximes can be prepared, for example, by reaction of a retinal with hydroxylamine, O-methyl- or O-ethylhydroxyl amine, or the like.

The synthetic retinal derivative can be substantially pure, in that it contains less than about 5% or less than about 1%, or less than about 0.1%, of other retinoids. A combination of synthetic retinal derivatives can be administered.

Synthetic retinal derivatives can be delivered to the eye by any suitable means, including, for example, oral, intravenous, intramuscular or local administration. Modes of local administration can include, for example, eye drops, intraocular injection or periocular injection, or delivery via a controlled release drug delivery formulation and/or device. Periocular injection typically involves injection of the synthetic retinal derivative into the conjunctiva or to the tennon (the fibrous tissue overlying the eye). Intraocular injection typically involves injection of the synthetic retinal derivative into the vitreous. The administration can be non-invasive, such as by eye drops or oral dosage form.

Synthetic retinal derivatives can be formulated, for example, as pharmaceutical compositions for local administration to the eye and/or for intravenous, intramuscular or oral administration.

Synthetic retinal derivatives can be formulated for administration using pharmaceutically acceptable vehicles as well as techniques routinely used in the art. A vehicle can be selected according to the solubility of the synthetic retinal derivative. Suitable pharmaceutical compositions include those that are administrable locally to the eye, such as by eye drops, injection or the like. In the case of eye drops, the formulation can also optionally include, for example, ophthalmologically compatible agents such as isotonizing agents such as sodium chloride, concentrated glycerin, and the like; buffering agents such as sodium phosphate, sodium acetate, and the like; surfactants such as polyoxyethylene sorbitan mono-oleate (also referred to as Polysorbate 80), polyoxyl stearate 40, polyoxyethylene hydrogenated castor oil, and the like; stabilization agents such as sodium citrate, sodium edentate, and the like; preservatives such as benzalkonium chloride, parabens, and the like; and other ingredients. Preservatives can be employed, for example, at a level of from about 0.001 to about 1.0% weight/volume. The pH of the formulation is usually within the range acceptable to ophthalmologic formulations, such as within the range of about pH 4 to 8.

Suitable pharmaceutical compositions also include those formulated for injection. For example, the synthetic retinal derivative can be provided in an injection grade saline solution, in the form of an injectable liposome solution, or other carriers or vehicles. Intraocular and periocular injections are known to those skilled in the art and are described in numerous publications including, for example, *Ophthalmic Surgery: Principles of Practice*, Ed., G. L. Spaeth, W. B. Sanders Co., Philadelphia, Pa., U.S.A., pages 85-87 (1990).

A synthetic retinal derivative also can be administered in a time release formulation and/or device, for example in a composition which includes a slow release polymer. The synthetic retinal derivative can be prepared with a carrier(s) that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

Suitable oral dosage forms include, for example, tablets, pills, sachets, or capsules of hard or soft gelatin, methylcellulose or of another suitable material easily dissolved in the digestive tract. Suitable nontoxic solid carriers can be used which include, for example, pharmaceutical grades of mannitol, lactose, starch, magnesium stearate, sodium saccharin, talcum, cellulose, glucose, sucrose, magnesium carbonate, and the like. (See, e.g., Remington *"Pharmaceutical Sciences"*, 17 Ed., Gennaro (ed.), Mack Publishing Co., Easton, Pa. (1985).)

The following examples are provided merely as illustrative of various aspects of the invention and should not be construed to limit the invention in any way.

EXAMPLES

Introduction

Both single dose and long-term monthly dosage regimens with 9-cis-R-Ac were used to assess the effect of artificial chromophore augmentation on the visual function of mice. The chromophore used was 9-cis-R-Ac, a pro-drug which is metabolized and converted to 9-cis-retinal to form isorhodopsin (Batten, M. L., et al. *PLoS medicine* 2, e333 (2005)). Twenty mice were employed for the single dose experiments (FIG. 1A, Table 1), whereas 210 were used for the long-term monthly treatments (FIGS. 1A, 1B, Table 1). Mice were also gavaged with all-trans-R-Ac (n=10) and its long-term effects was evaluated by selected analyses.

Abbreviations 9-cis-R-Ac, 9-cis-retinyl acetate; A2E, N-retinylidene-N-retinyl ethanolamine; ERG, electroretinogram; LRAT, lecithin:retinol acyltransferase; ROS, rod outer segments; RPE, retinal pigment epithelium; RPE65, a RPE-specific 65 kDa protein.

Example 1

Single Dose Treatment of C57BL/6 Female Mice with 9-cis-R-Ac

Figures 3A, 3B, 3C:
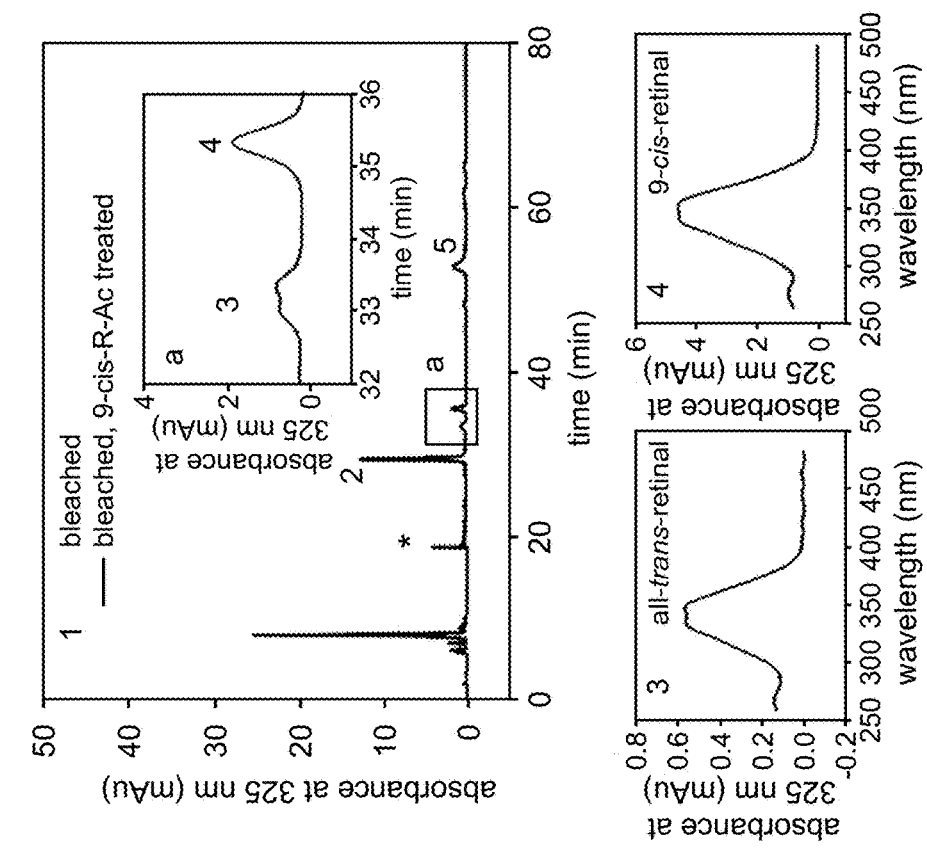
FIGS. 3A-3C. Retinoid levels in eyes from 9-cis-R-Ac gavaged mice exposed to intense light followed by full dark-adaptation.

Forty eight hr dark-adapted, 10-month-old mice were gavaged with a single dose (~80 mg/kg body weight) of 9-cis-R-Ac or control vehicle and exposed to strong illumination for 20 min (500 cd·m$^{-2}$ that bleached ~90% rhodopsin). Next, mice were dark-adapted for 16 hr after which various analyses were performed (FIG. 1A). Single-flash ERG conducted on treated and untreated mice showed that functional a- and b-wave amplitudes of treated mice were slightly increased as compared with the amplitudes in control mice (a-waves, P<0.01; data not shown). To investigate whether 9-cis-retinal was utilized to form isorhodopsin and to assess how much unliganded opsin was present in the mouse eyes, rhodopsin, isorhodopsin and opsin were purified by immunoaffinity chromatography from treated and control groups of mice. The regeneration ratio of rhodopsin was calculated by the ratio of rhodopsin and isorhodopsin (absorbance at 498 nm) to purified protein (absorbance at 280 nm) in each fraction, was significantly higher in eyes from treated than from control mice whereas the total amount of purified protein did not significantly differ (FIG. 2). When retinoids were extracted from purified proteins to identify bound chromophore, a significant amount of 9-cis-retinal was detected in samples from treated mice, suggesting that 9-cis-retinal was utilized to regenerate opsin to form isorhodopsin (data not shown). Significant amounts of 9-cis-retinal were detected in eyes of exposed to intense light and treated mice (FIGS. 3A and 3B), whereas the amounts of 11-cis-retinal and all-trans-retinyl esters were not significantly affected in all groups of mice (FIGS. 3B and 3C). In these treated and exposed to intense light mice, the RPE also stored significant amount of 9-cis-retinyl esters, a precursor of the retinal (FIG. 3C). Only trace amounts of 9-cis-retinal were detected in control mouse eyes and unbleached treated mouse eyes (FIGS. 3B and C). These results clearly demonstrate that 9-cis-R-Ac is metabolized its esters to form functional 9-cis-retinal and in wild-type C57BL/6 female mice. After bleaching, 9-cis-retinal is bound to opsin even in the presence of a functional retinoid cycle that produces 11-cis-retinal to regenerate rhodopsin. Eyes from non-bleached or bleached and dark-adapted untreated mice contained a small amount of free opsin.

Example 2

Long-Term Treatment of C57BL/6 Female Mice with 9-cis-R-Ac

For the long-term studies (FIGS. 1B and 1C), C57BL6 female mice were gavaged with 9-cis-R-Ac, all-trans-R-Ac or control vehicle monthly for 6 or 10 months.

Example 3

Single Flash ERG Analyses

Figure 4A:
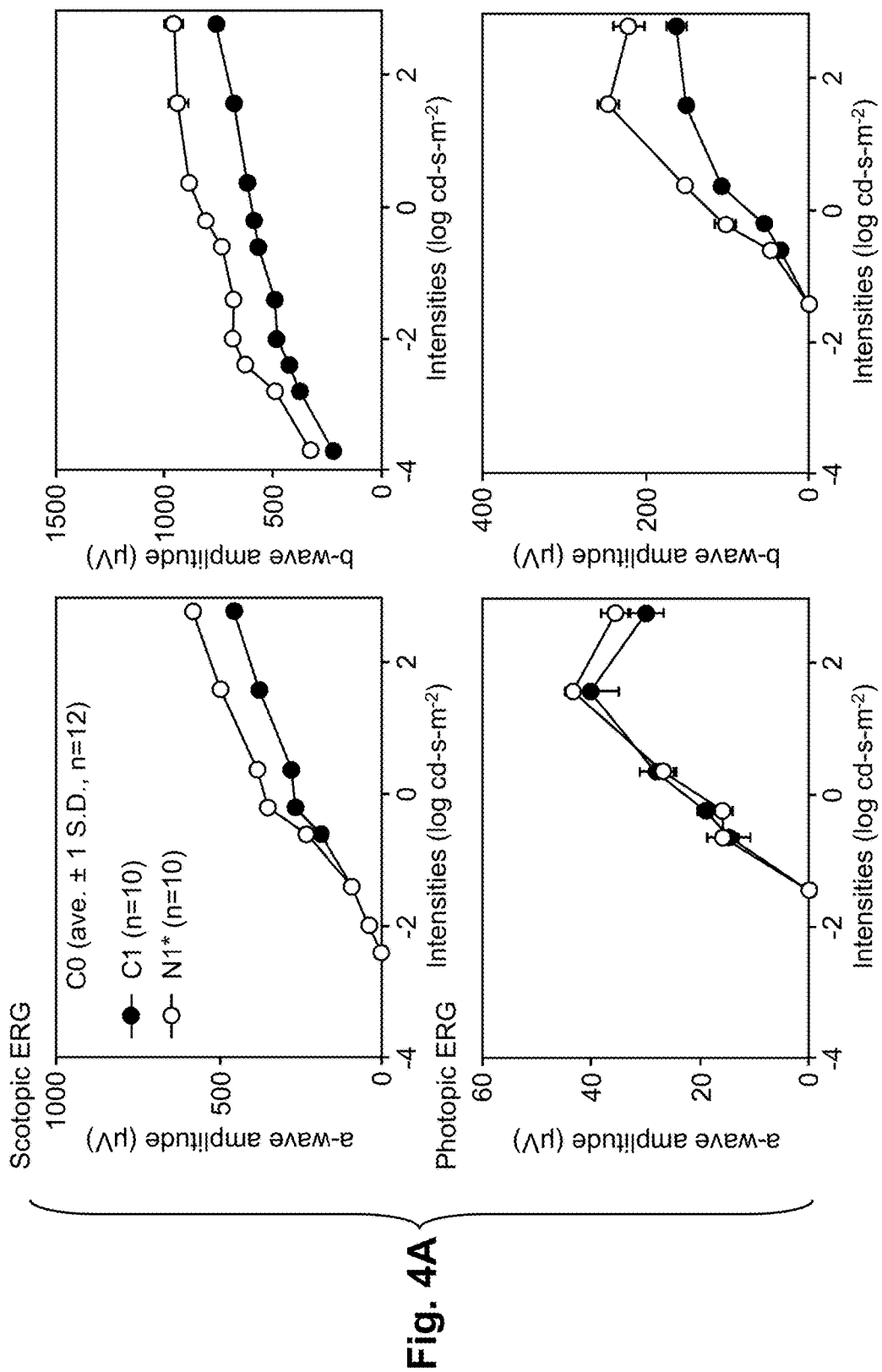
FIGS. 4A and 4B. ERG analysis of control and long-term 9-cis-R-Ac treated mice.

To evaluate the effects of rod- and cone-mediated light responses after long-term 9-cis-R-Ac treatments, mice were examined by non-invasive ERG methods. The first set of analyses was done at 4 and 10 months of age. Under scotopic conditions, the amplitudes of a-waves decreased with age, especially at high flash intensities (C1 versus C0 group, FIG. 4A, left top panel), whereas the changes in b-waves were less evident (FIG. 4A, right top panel). Under photopic conditions, no differences were observed for either a- or b-waves (FIG. 4A, lower panels). When treated and untreated groups were compared (N1 versus C1) slight improvement was observed for the N1 group with respect to a- or b-waves at high flash strengths ($p<0.01$, one-way ANOVA) under both photopic and scotopic conditions with the exception of a-waves under photopic conditions (FIG. 4A, left lower panels).

Figure 4B:
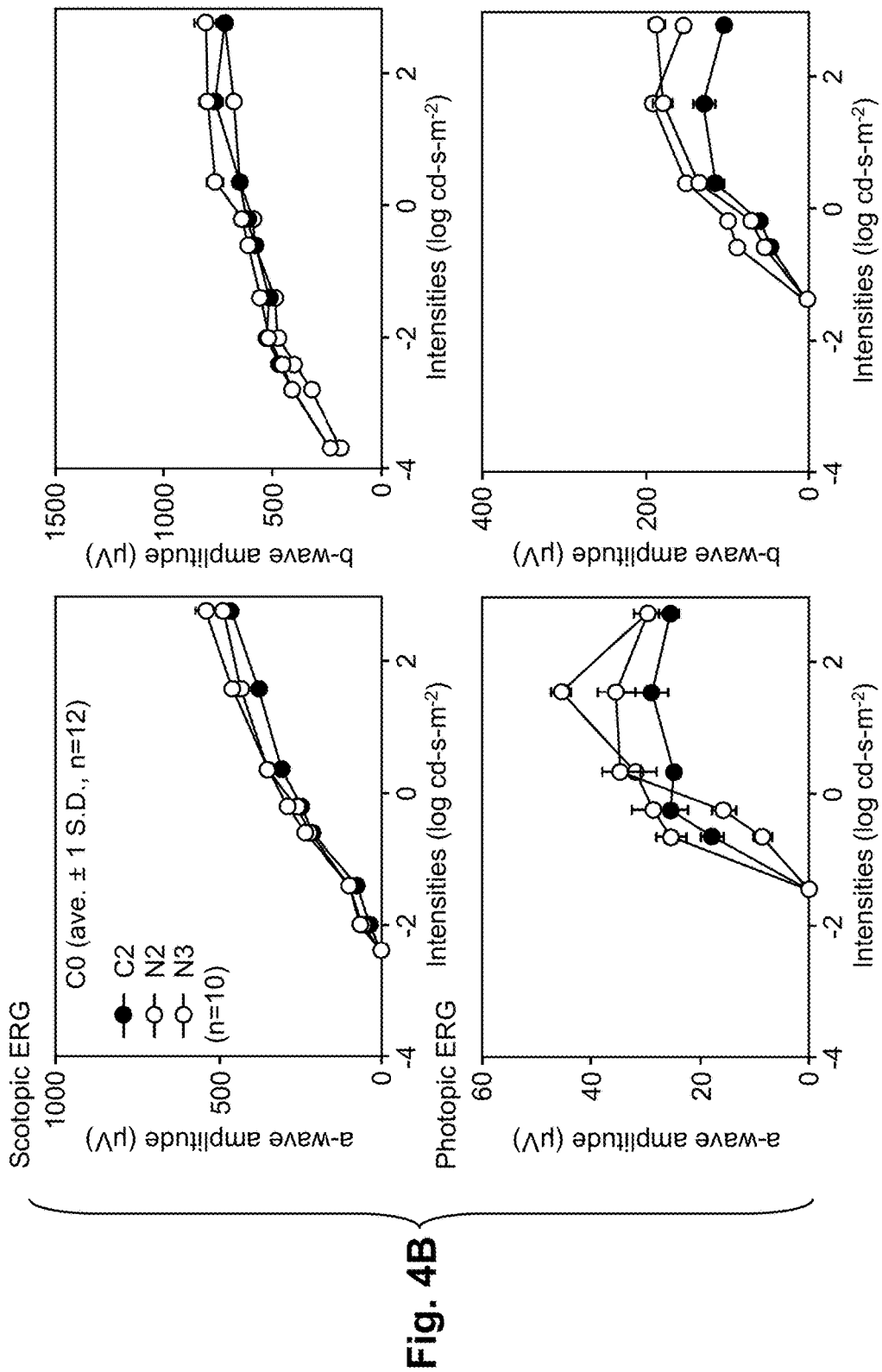

The second set of analyses was done at 14 months of age. No significant differences were found in a- and b-wave amplitudes between control (C2) and treated groups of mice (N2 and N3) under either scotopic of photopic conditions (FIG. 4B). From a-wave maximal responses in dark-adapted mice, sensitivities and maximal a-wave amplitudes were estimated and these parameters were found not to be significantly different either (data not shown).

Example 4

Changes in Dark Adaption

Recovery of the ERG response (dark adaptation) following bleach was measured by monitoring the amplitude of a-waves after retinal exposure to intense constant illumination (500 cd·m$^{-2}$, ~90% bleached rhodopsin) for 3 min. Recovery of the responses was significantly faster in the 9-cis-R-Ac treated groups compared with the control groups of mice at both 10 months (N1 vs. C1, FIG. 5A) and 14 months of age (N2 and N3 vs. C2, FIG. 5B)($p<0.001$, one-way ANOVA). Retinoid kinetics in the eyes of each group were quantitatively evaluated during 60 min of dark adaptation after 3 min of bleaching at four subsequent time points of dark adaptation (0, 10, 30, and 60 min). At 10 months of age, the regeneration level of 11-cis-retinal in a treated group (N1) was significantly higher than in the control group (C1) ($p<0.01$) 60 min after the bleach. But there was no significant difference in kinetics of all-trans-retinal and all-trans-retinyl-esters between these groups and between treated and untreated mice at 14 months of age. Neither 9-cis-retinal nor 9-cis-retinyl esters were found in eyes from untreated groups (data not shown).

Example 5

Effects of Long-Term Administration of all-trans-R-Ac on Visual Function

In additional control experiments, mice were gavaged with an inactive isomer, all-trans-R-Ac (n=10) for 10 months and evaluated at 14 months age. ERG examination showed no significant difference compared with control (C2) in single flash ERG a- and b-wave analyses or in dark adaptation recovery (n=3). These results showed that ERG effects are specific for 9-cis isomer.

Example 6

Analyses of Rhodopsin, A2E and Retinoid Acids in Control and 9-cis-R-Ac Treated Mice Regeneration ratios (rhodopsin/opsin) and total amounts of purified rhodopsin showed no significant differences between control and treated groups of mice at both 10 and 14 months of age. The amounts of purified protein recovered from the treated groups at 14 months of age (N2 and N3) were significantly lower than these from control mice (C2), whereas the amount was only slightly attenuated in at 10-month-old treated mice (N1 versus C1) (data not shown).

Figures 6A, 6B:
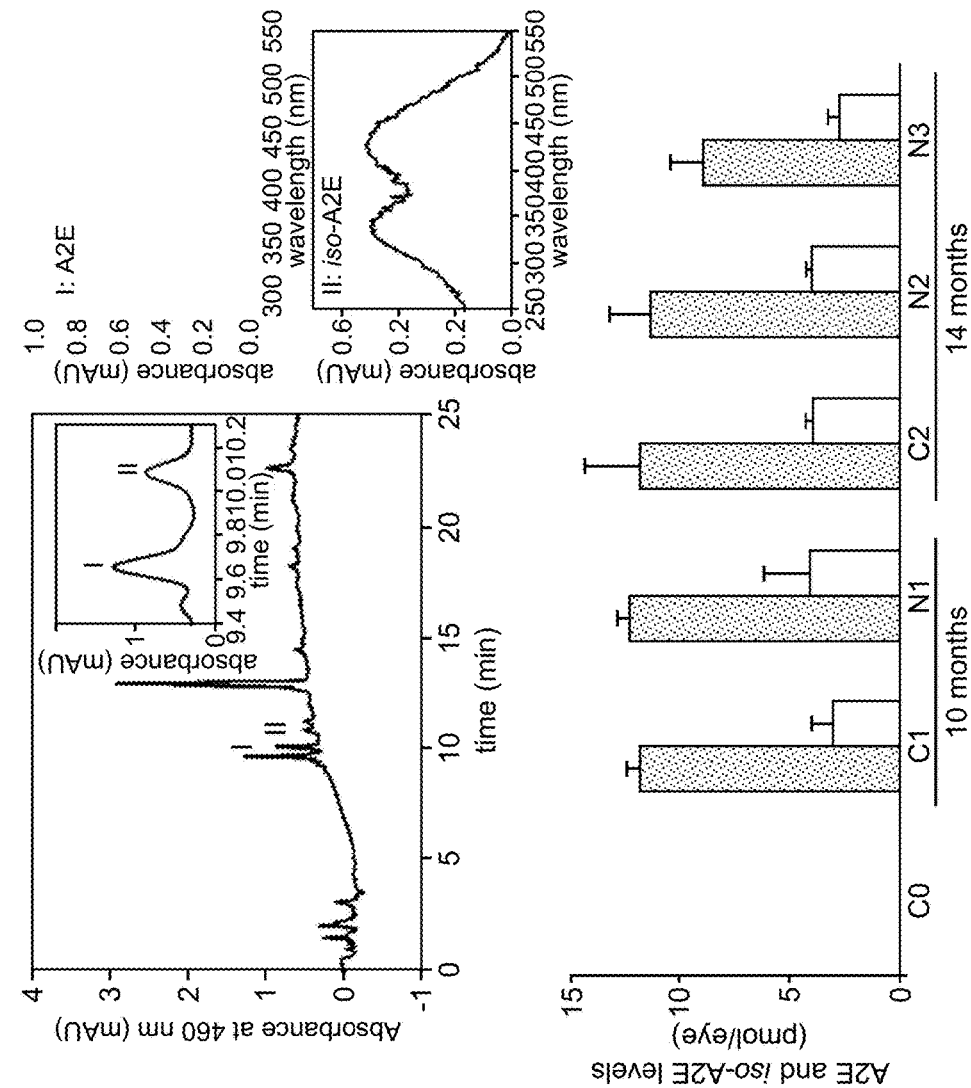
FIGS. 6A and 6B. A2E accumulation in the eyes of control and long-term 9-cis-R-Ac treated mice.

To evaluate the safety of long-term administration of 9-cis-R-Ac, A2E accumulation was measured (FIG. 6A), because retinals spontaneously condense to this compound (Mata, N. L., Weng, J. & Travis, G. H. *Proceedings of the National Academy of Sciences of the United States of America* 97, 7154-7159 (2000); Parish, C. A., Hashimoto, M., Nakanishi, K., Dillon, J. & Sparrow, J. *Proceedings of the National Academy of Sciences of the United States of America* 95, 14609-14613 (1998)). A2E and iso-A2E were detected at similar levels in treated and control mice at both 10- and 14 months of age (FIG. 6B). In pre-treatment controls (C0, 4 months old), A2E accumulation was below detectable levels (FIG. 6B). Although long-term treatment with retinyl esters might produce elevated levels of mitogenic retinoic acid in the liver, hepatic retinoid-acid levels were below detectable levels in all groups (data not shown).

Example 7

Husbandry and Morphology of Retinas from 9-cis-R-Ac Treated Mice

Animals were evaluated weekly for activity and changes in coat and skin appearance. No changes in these parameters were observed during the experimental period aside from these due to natural aging. Body weights of mice evaluated at pre-treatment, 10 months and 14 months showed no significant differences between control (C1-2) and treated groups (N1-3) (data not shown).

Figure 7:
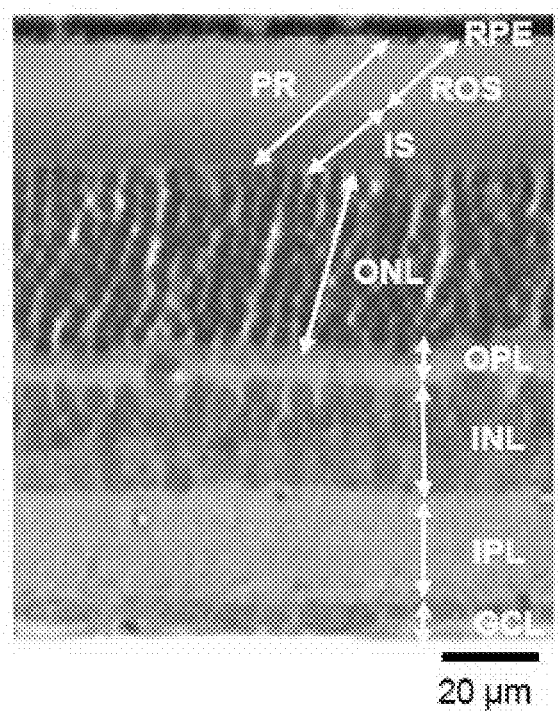
FIG. 7. Retinal morphology of 9-cis-R-Ac gavaged mice. A representative cross-section of a 4-month-old untreated mouse (C0) is shown. RPE, retinal pigment epithelium; PR, photoreceptors, ROS, rod outer segment; IS, inner segment; ONL, outer nuclear layer; OPL, outer plexiform layer; INL, inner nuclear layer; IPL, inner plexiform layer; and GCL, ganglion cell layer.

Light microscopy revealed no major abnormalities in the retinas of vehicle, 9-cis-R-Ac or all-trans-R-Ac (n=2) treated mice at 10 and 14 months of age and retinas from these two 9-cis-R-Ac treated groups were indistinguishable. Lengths of rod outer segments (ROS) were similar in control and treated groups at 10- and 14 months of age but were significantly decreased as compared to ROS lengths of 4-month-old mice (C0) whose retinal histology is shown in FIG. 7. The thickness of each major layer in the retina was also similar between control and treated groups. EM analysis of the outer retina and RPE layer revealed no gross differences between control and treated mice. Higher resolution of the interface between the RPE and ROS also showed no abnormalities (data not shown).

Example 8

Changs in DNA Expression Profiles with 9-cis-R-Ac Administration

Figure 8:
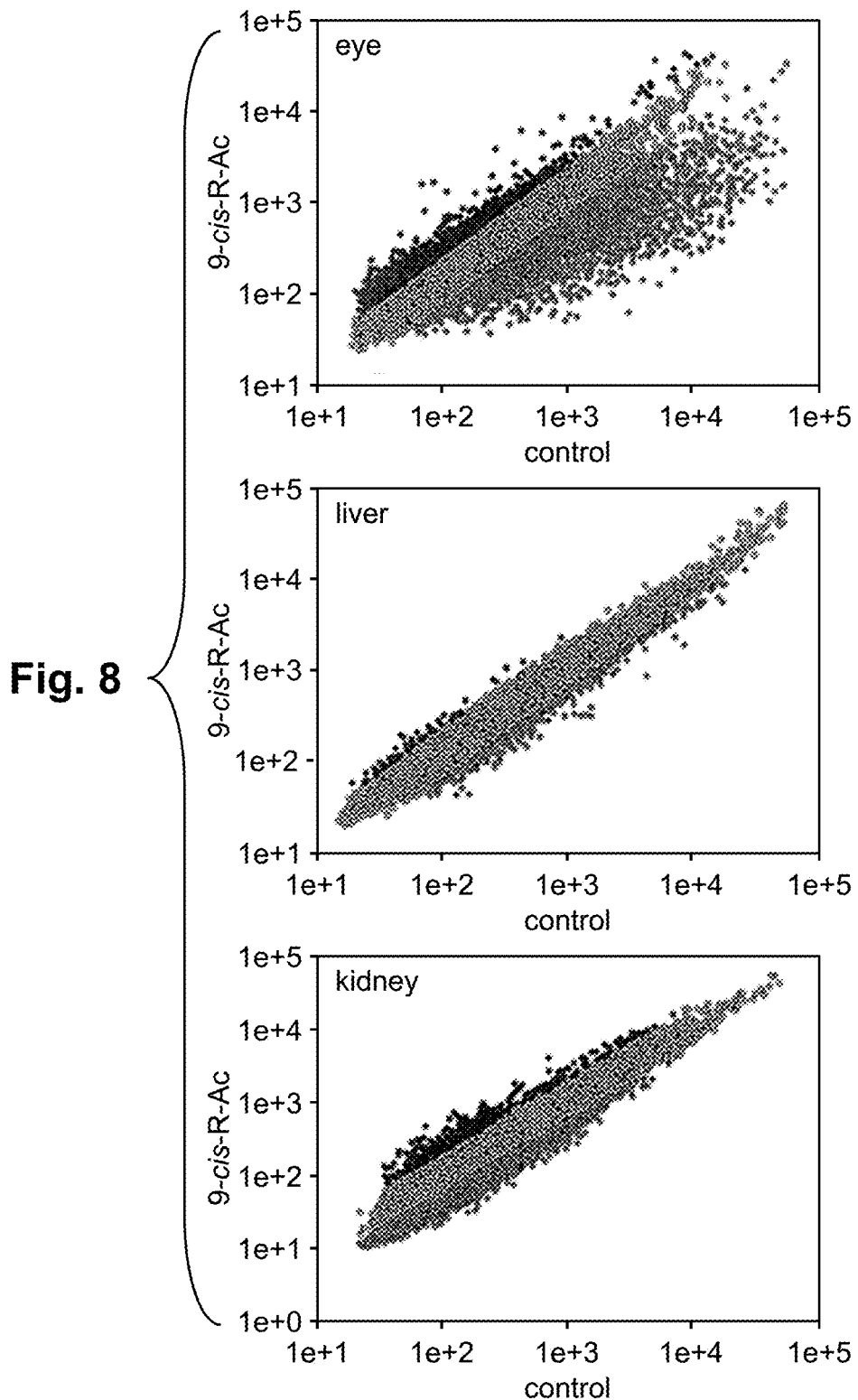
FIG. 8. RNA array analyses of control and long-term 9-cis-R-Ac treated mice. Expression levels of 37,364 genes from the eye, liver and kidney of two groups of mice, C2 and N2, were examined by cDNA arrays (provided by Nimblegen). Two independent RNA samples were prepared for microarray hybridization. Normalized values of mRNA expression were plotted (control vs. each 9-cis-R-Ac treated group, Examples—Methods section) as scatter plots with Sigma Plot v9.0. Genes expressed more than 2.0 fold and less than 0.5 fold are indicated in red and blue respectively. Further information is available from supplemental Tables S1 and S2. Immunoblots of eye extracts from different groups of mice were probed with various antibodies as described in the Examples—Methods section.

DNA microarray analyses were used to document possible changes in gene expression profiles after the long-term treatment with 9-cis-R-Ac. Expression levels of mRNA in the eye, liver and kidney were determined and compared between treated (N2) and control (C2) groups using a 37,364 gene array provided by NimbleGen System Inc. In the eye, 9-cis-R-Ac treatment elevated expression of 290 genes by a factor of 2 or more and attenuated expression of more than 1057 genes by a factor of 0.5 or less (FIG. 8; Table S1). In the liver of treated mice, expression of only 7 genes was increased by a factor of 2 or more and expression of only 20 genes was suppressed by a factor of 0.5 or less (FIG. 8; Table S2). In the kidney of treated mice, 90 genes increased their expression by a factor of 2 or more and 3 genes suppressed it by a factor of 0.5 or less (FIG. 8; Table S2). The phototransduction-specific, retinoid processing and function-categorized genes whose expressions were affected in the eye are listed in Tables S2. Protein levels of transducin (Gt), rhodopsin kinase, guanylate cyclase-activating protein 1 and guanylate cyclase-activating protein 2, guanylate cyclase 1, retinol dehydrogenase 12 and LRAT were not affected in all groups of mice as assessed by immunoblotting (data not shown).

TABLE 1

Numbers of mice utilized for experimental analyses in the single and long-term dosage studies of 9-cis-R-Ac treatment.

| Study Type | ERG | Retinoid analysis | Rhodopsin characterization | A2E analysis[a] | mRNA analysis | Histology[a,b] |
|---|---|---|---|---|---|---|
| single dose treatment | 4 | 3 | 3 | — | — | — |
| long-term treatment | 10 | 15 | 5 | 5 | 4 | 5 |

[a]Mice were used after ERG tests for these experiments.
[b]One eye from a mouse was used for light microscopy and the other for electron microscopy.

Discussion

As shown in these studies, age-related deterioration of dark adaptation in mice is attenuated by artificial cis-retinoid treatment. This finding is analogous to age-related declines in human vision manifested by the dramatic slowing of rod-mediated dark adaptation directly attributed to delayed rhodopsin regeneration (Jackson, G. R., Owsley, C. & McGwin, G., Jr. Vision Research 39, 3975-3982 (1999)). Two different types of studies were done. Single dose studies revealed that 9-cis-retinoids could enter the eye, and a second set of experiments showed that long-term administration of 9-cis-R-Ac significantly improved the deterioration of retinal function in aging mice.

Single Dose Experiments

These experiments were designed to test whether 9-cis-retinoids enter the eyes of 10-month-old mice and improve visual function. The ERG response measurably declined with age and small but measurable amounts of free opsin was present in these old mice. 9-cis-retinal entered the eye when these treated mice were exposed to intense light and tested 18 hr later. The precursors of 9-cis-retinal, 9-cis-retinyl esters, were easily detectable in the eyes of these mice and the rhodopsin/opsin ratio improved as well.

Long-Term Treatment of Mice with 9-cis-R-Ac

Figure 5B:
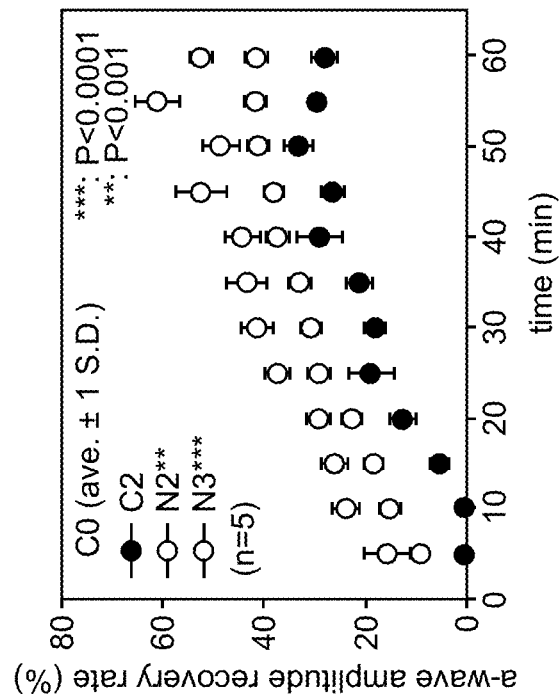
FIGS. 5A and 5B. Recovery of dark adaptation in control and long-term 9-cis-R-Ac treated mice after intense light bleaching.
Figure 5A:
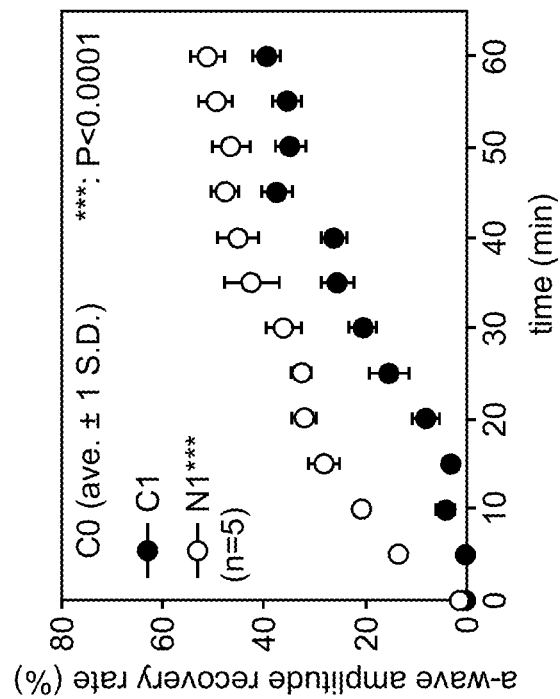

ERG responses to a single light flash were significantly improved in 10-month-old mice that were treated for 6 months with 9-cis-R-Ac as compared with the oil-treated controls (FIG. 4A). This therapeutic effect largely disappeared in 14-month-old mice treated for 10 months (FIG. 4B), possibly due to the masking effect of debilitation in the older mice. However, these older mice did display a significant effect involving dark adaptation (FIG. 5B, N2 and N3 groups). That long-term gavage of 14-month-old mice with all-trans-R-Ac had no effect on measured ERG parameters is not surprising because only the cis-form of the chromophore can recombine with opsin (reviewed in Palczewski, K. Annual Review of Biochemistry 75, 743-767 (2006); Filipek, S., Stenkamp, R. E., Teller, D. C. & Palczewski, K. Annu Rev Physiol 65, 851-879 (2003)). Thus, all-trans-retinoid would only add substrate for the isomerization reaction but not supplement the active chromophore if isomerization was attenuated. Importantly, mice in captivity are maintained on high vitamin A diet, thus observed effects of cis-retinoids is already on the top of all-trans-retinoid supplementation.

Long-term treatment (6-10 months) was well tolerated by C57BL/6 female mice. Age-related detectable morphological changes in the retina were observed in both treated and control mice were not affected by treatment. Potential toxic by-products of retinoid treatment, A2E and retinoic acid, did not accumulate in these mice. In this study, 9-cis-R-Ac was incorporated into free-opsin within the retina resulting in increased regeneration ratio of rod pigments. However, the amount of all-trans-retinal induced by physiological light conditions is constant regardless of the amounts of rod pigments and the regeneration ratio. Therefore, it is not surprising that A2E levels were not affected by 9-cis-R-Ac administration. Thus, the beneficial effect of cis-retinoid supplementation seems more advantageous from this perspective than from the anti-oxidant properties generally attributed to retinoids (Maxwell, S. & Greig, L. Expert Opinion on Pharmacotherapy 2, 1737-1750 (2001)).

We did not detect any accumulation of retinoic acids. Moreover, gene expression changes were minimal in the liver and kidney while several proteins were unregulated in the eye. Our detailed analysis of these genes did not reveal any particular expression patterns.

Prophylactic Use of 9-cis-retinoids

Humans begin to lose their ability to dark adapt beginning in the $3^{rd}$-$4^{th}$ decade (Jackson, G. R., McGwin, G., Jr., Phillips, J. M., Klein, R. & Owsley, C. Vision Research 46, 1422-1431 (2006)). A decline in the visual function is functionally manifested by reduction in the ability to perform activities such as driving at night and reading in darkened environments (Schilling, O. K. & Wahl, H. W. Psychology and aging 21, 703-714 (2006)). Such symptoms become more debilitating with age and can result in reduced independence and activity in the elderly. The problem becomes more acute as people live longer. Results of our experiments demonstrate that oral 9-cis-retinoid is useful as a long-term prophylactic agent and as a therapeutic compound.

The beneficial effects and relative safety of 9-cis-retinoids extends to age-related macular degeneration, the leading cause of legal blindness in the U.S. and Europe (Zack, D. J., et al., Mol Vis 5, 30 (1999)). Here, we have shown that there are biochemical changes in the visual cycle that occur with age, namely an increase in free opsin and the opsin/rhodopsin ratio. When such biochemical changes are excessive they can lead to retinal degenerations such as seen in LCA (Fan, J., Woodruff, M. L., Cilluffo, M. C., Crouch, R. K. & Fain, G. L. J Physiol 568, 83-95 (2005)). In addition, free opsin results in spontaneous initiation of the visual cascade in rod photoreceptors (Lisman, J. & Fain, G. Nat Med 1, 1254-1255 (1995); Fain, G. L., Matthews, H. R., Cornwall, M. C. & Koutalos, Y. Physiol Rev 81, 117-151 (2001); Surya, A., Foster, K. W. & Knox, B. E. J Biol Chem 270, 5024-5031 (1995); Hofmann, K. P., Pulvermuller, A., Buczylko, J., Van Hooser, P. & Palczewski, K. J Biol Chem 267, 15701-15706 (1992); Palczewski, K., et al. Biochemistry 33, 13741-13750 (1994); Jager, S., Palczewski, K. & Hofmann, K. P. Biochemistry 35, 2901-2908 (1996)). This results in a decreased signal-to-noise ratio in the visual system, increased metabolic overload in the RPE, resulting in the formation of more waste products, free radicals and, eventually, drusen. Decreasing free opsin with 9-cis-retinoid therapy will therefore lead to a reduction in the precursors that are believed to initiate AMD.

Methods

Animals

Pigmented age-matched C57BL/6 female mice obtained from Charles River Laboratories were maintained on a normal diet in complete darkness or on a 12-hr light/dark cycle. All animal experiments utilized procedures approved by the University of Washington and Case Western Reserve University Animal Care Committees and conformed to recommendations of the American Veterinary Medical Association Panel on Euthanasia and the Association of Research for Vision and Ophthalmology.

Single Dose and Long-Term Treatment of Mice with 9-cis-R-Ac 9-cis-R-Ac was prepared as previously described (Batten, M. L., et al. *PLoS medicine* 2, e333 (2005); Batten, M. L., et al. *J Biol Chem* 279, 10422-10432 (2004)). A dose of ~80 mg/kg body weight of 9-cis-R-Ac in 150 μl vegetable oil was administered via gavage to each treated animal. Prior to single dose experiments (FIG. 1A, Table 1), 10-month-old mice were dark-adapted for more than 48 hr, gavaged with 9-cis-R-Ac or vehicle control solution 1 hr before bleaching, exposed to light for 20 min at 500 cd·m$^{-2}$ and dark-adapted for 16 hr before analysis.

For the long-term study (FIGS. 1B and 1C, Table 1), mice were obtained at 3 months of age and raised until 4 months of age before the experiments were initiated. Mice then were gavaged with 9-cis-R-Ac or vehicle solution once a month for different durations. Six groups of mice were studied (FIG. 1B). The first 3 groups (C0 C1 and C2, total n=35 for each group) were treated as controls and tested at 4, 10 and 14 months of age. The other 3 groups (N1, N2 and N3, n=35) were gavaged with 9-cis-R-Ac. Group N1 was gavaged for 6 months and tested at 10 months of age. Group N2 was gavaged with 9-cis-R-Ac for 10 months and tested at 14 months of age. Group N3, was gavaged with vehicle until 10 months of age and then received 9-cis-R-Ac monthly until testing at 14 months of age. In another control group not shown in FIG. 1B, 10 mice were gavaged with ~80 mg/kg body weight of all-trans-R-Ac (Sigma-Aldrich, Corp.) for 10 months and tested at 14 months of age.

Two weeks after the last gavage with either, 9-cis-R-Ac, all-trans-R-Ac or vehicle, groups of 48 hr dark-adapted mice were analyzed for recovery of dark adaptation after light exposure, purified rhodopsin/opsin and retinoids in the eye and retinal morphology (FIG. 1C; Methods). Mice were exposed to light of intensity 500 cd·m$^{-2}$ that bleached ~90% of rhodopsin, anesthetized and monitored by ERG for one hr to evaluate recovery of dark adaptation. Rhodopsin was purified and rhodopsin/opsin ratios was determined. Retinoid analyses were performed on dissected eyes removed at 0, 10, 30, and 60 min after exposure to the same amount of light. Mice used to evaluate retinal morphology were not exposed to photobleaching prior to analysis.

Electroretinography (ERG)

ERGs of anesthetized mice were recorded as previously reported.

Purification of Rhodopsin

Rhodopsin purification was done under dim red light as previously described (Zhu, L., et al. *J Biot Chem*, 279, 53828-53839 (2004)). Purified anti-rhodopsin C terminus antibody 1D4 (MacKenzie, D., Arendt, A., Hargrave, P., McDowell, J. H. & Molday, R. S. *Biochemistry*, 23, 6544-6549 (1984)) was immobilized on CNBr-activated Sepharose 4B and a 4.6×12-mm column was packed with 2 mg of 1 D4 antibody/ml of Sepharose beads. Mouse whole eyes were homogenized in 137 mM NaCl, 5.4 mM Na$_2$HPO$_4$, 2.7 mM KCl and 1.8 mM KH$_2$PO$_4$ (pH 7.5) with a glass-to-glass homogenizer. Soluble proteins in the supernatant were removed by centrifugation at 14,000×g for 5 min and the pellet was solubilized in buffer containing 1% dodecyl-β-maltoside in 10 mM Bis-Tris propane (pH 7.5) containing 500 mM NaCl. The supernatant was cleared by centrifugation at 125,000×g for 20 min and loaded onto an antibody 1 D4-packed immunoaffinity column which was then thoroughly washed at a flow rate of 0.5 ml/min with 10 mM Bis-Tris propane (pH 7.5) containing 500 mM NaCl and 0.1% dodecyl-β-maltoside. Purified mouse rhodopsin was eluted with 100 μM nonapeptide (TETSQVAPA) in 10 mM Bis-Tris propane (pH 7.5) containing 500 mM NaCl and 0.1% dodecyl-β-maltoside at room temperature. Purified rhodopsin concentration was determined at 500 nm and total amount of opsin and rhodopsin at 280 nm with a Hewlett-Packard 8452A UV-visible spectrophotometer (Palczewski, K., Carruth, M. E., Adamus, G., McDowell, J. H. & Hargrave, P. A. *Vision Research*, 30, 1129-1137 (1990)).

Analysis of Retinoids

All experimental procedures related to extraction, derivatization and separation of retinoids were carried out under dim red light provided by a Kodak No. 1 safelight filter (transmittance>560 nm) as described previously (Van Hooser, J. P., et al. *Proceedings of the National Academy of Sciences of the United States of America* 97, 8623-8628 (2000); Van Hooser, J. P., et al. *J Biol Chem*, 277, 19173-19182 (2002); Maeda, A., et al. *J Biol Chem* 280, 18822-18832 (2005); Van Hooser, J. P., Garwin, G. G. & Saari, J. C. *Methods Enzymol* 316, 565-575 (2000)). Eluted fractions of purified rhodopsin from 6 mouse eyes were combined (total 3.0 ml) and mixed with an equal volume of 100% methanol. The mixture was vortexed and incubated on ice for 15 min. Retinoids were extracted twice with an equal volume of 100% hexane (6 ml total). The combined extracts were dried under argon and retinoids were separated by normal phase HPLC (Beckman, Ultrasphere-Si, 5 μm, 4.6× 250 mm) with 10% ethyl acetate and 90% hexane at a flow rate of 1.4 ml/min and detected at 325 nm by an HPI 100 HPLC with a diode array detector and HP Chemstation A.03.03 software. A2E was analyzed as previously described (Maeda, A., et al. *J Biol Chem*, 280, 18822-18832 (2005)).

Analysis of retinoic acid in the liver was carried out as described before (Batten, M. L., et al. *PLoS Medicine* 2, e333 (2005)) by an Agilent 1100 HPLC with two tandem normal phase columns: a Varian Microsorb Silica 3 μm, 4.6×100 mm (Varian, Palo Alto, Calif.) and an Ultrasphere-Si, 5 μm, 4.6×250 mm column. An isocratic solvent system of 1000:4.3:0.675 hexane:2-propanol:glacial acetic acid (v/v) was used at a flow rate of 1 ml/min at 20° C. with detection at 355 nm. Calibration was done with standards of all-trans-RA and 9-cis-RA purchased from Sigma-Aldrich.

Immunoblotting

Immunoblotting was done according to standard protocols using Immobilon-P to adsorb proteins (polyvinylidene difluoride; Millipore Corp.). Monoclonal anti-rhodopsin antibody (1D4) was provided by Dr. R. Molday. The anti-LRAT (mAb) (Moise, A. R., Golczak, M., Imanishi, Y. & Palczewski, K., *J Biol Chem* (2006)), anti-transducin (Gt) (mAb) (unpublished), anti-guanylate cyclase 1 (1S4, mAb); Haire, S. E., et al. *Investigative ophthalmology & visual science* 47, 3745-3753 (2006)), anti-guanylate cyclase-activating protein 1 (UW14 pAb) (Gorczyca, W. A., et al. *J Biol Chem*, 270, 22029-22036 (1995)), anti-guanylate cyclase-activating protein 2 (UW50 pAb) Otto-Bruc, A., et al. *Proceedings of the National Academy of Sciences of the United States of America* 94, 4727-4732 (1997)), anti-rhodopsin kinase (Zhao, X., Huang, J., Khani, S. C. & Palczewski, K. *J Biol Chem* 273, 5124-5131 (1998)), and anti-retinol dehydrogenase 12 (pAb) (Maeda, A., et al. *J Biol Chem* 281, 37697-37704 (2006)) were generated in our laboratory. Alkaline phosphatase-conjugated goat anti-mouse IgG or goat anti-rabbit IgG (Promega) were used as secondary antibodies. Protein bands were visualized with 5-bromo-4-chloro-3-indolyl phosphate/nitro blue tetrazolium color development substrate (Promega). Proteins (30 µg per each well) were separated by 12.5% SDS-PAGE.

Retinal Morphology

For light microscopy, mouse eyecups were fixed with 2.5% glutaraldehyde and 1.6% paraformaldehyde in 0.08 M 1,4-piperazinediethanesulfonate buffer (PIPES) (pH 7.4) containing 2% sucrose for ~1 hr at room temperature followed by 23 hr at 4° C. Eyecups then were washed with 0.13 M sodium phosphate buffer (pH 7.3) and dehydrated through a $CH_3OH$ series and embedded in JB4 glycol metacrylate. Sections (6 µm) were stained by immersion in 5% Richardson's stain for 1.5-2 min at room temperature and destained in 0.13 M sodium phosphate (pH 7.3) until the retinal layers were visible by light microscopy (about 8-15 min). For transmission electron microscopy, mouse eyecups were analyzed as described previously (Maeda, A., et al. *J Blot Chem* 280, 18822-18832 (2005); Maeda, T., Lem, J., Palczewski, K. & Haeseleer, F. *Investigative ophthalmology & visual science* 46, 4320-4327 (2005)).

DNA Microarray Analysis

RNA was isolated from 10 eyes, 100 mg of liver or 100 mg of kidney from groups C2 and N2 mice (FIG. 1B) with a RiboPure Kit (Ambion, Austin, Tex.). Quality of the preparation was verified by RNA agarose gel electrophoresis and the Agilent Bioanalyzer. Aliquots of total RNA isolated from the different tissues and from mice undergoing various treatments were detection-labeled and hybridized on the mouse genomic microarray using a service provided by NimbleGen System Inc. (Madison, Wis.). The microarray contained the 37,364 genes and covering the entire mouse transcriptome as represented by the University of California, Santa Cruz database (build HG 17) with a minimum of 11 probes per gene. Gene expression was normalized according to probe signal, and the average signal for each gene was normalized for each sample replicate.

Array data for samples across the whole study were normalized by NimbleGen Systems Inc. (Madison, Wis.) that employed the robust multichip analysis feature of the data analysis package contained in the Bioconductor open source and open development software project for the analysis and comprehension of genomic data. Project-wide spreadsheets of robust multichip analysis results were exported to MICROSOFT® EXEL® and expression level ratios were calculated for all the possible pair-wise comparisons comprising one control and one treated sample. These pair-wise ratios were imported to Microsoft Access and mined for credible-fold changes in gene expression. Changes greater than or equal to a 2-fold increase or less than or equal to a 0.5-fold decrease were considered significant. Differentially expressed genes were then exported from Access as Excel files and were assigned functional annotations by LUCIDYX SEARCHER™ software by Lucidyx LLC.

Statistical Analyses

Statistical analyses were performed by one-way analysis of variance (ANOVA).

The previous examples were provided to illustrate but not to limit the scope of the claimed inventions. Other variants of the inventions will be readily apparent to those of ordinary skill in the art and are encompassed by the appended claims.

All publications, patents, patent applications and other references cited herein are hereby incorporated by reference, as allowed.

The invention claimed is:

1. A method of treating age-related macular degeneration (AMD) in a human subject, comprising:
administering a therapeutically effective amount of a synthetic retinal derivative to the human subject, wherein the synthetic retinal derivative supplements or replaces endogenous 11-cis-retinal in the eye, wherein the synthetic retinal derivative is administered orally as a long term dosage regimen about once every other day to about once a month for about four months or longer; wherein the synthetic retinal derivative is a 9-cis-retinyl ester having a structure as represented by Formula I, and wherein A is $CH_2OR$ and —R, along with the adjacent oxygen, forms a retinyl ester, and the ester substituent comprises a carboxylate radical of a $C_1$ to $C_{10}$ monocarboxylic acid or a $C_2$ to $C_{22}$ polycarboxylic acid:

Formula I:

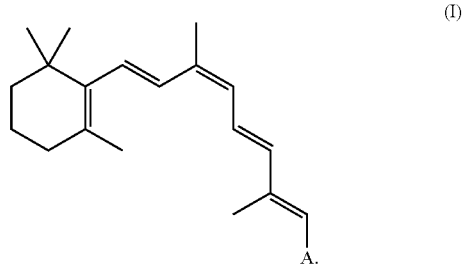

(I)

2. The method of claim 1, wherein the synthetic retinal derivative is administered about once a month over a period of at least four months.

3. The method of claim 1, wherein the synthetic retinal derivative is administered about 2-4 times per week to about once every month for at least four months.

4. The method of claim 1, wherein the long term dosage regimen is administered about once every two weeks over a period of at least four months.

5. The method of claim 1, wherein the ester substituent is a carboxylate radical of a monocarboxylic acid of $C_1$ to $C_{10}$.

6. The method of claim 1, wherein the ester substituent is a carboxylate radical of a polycarboxylic acid of $C_3$ to $C_{10}$.

7. The method of claim 1, wherein the synthetic retinal derivative is selected from 9-cis-retinyl acetate, 9-cis-retinyl succinate, 9-cis-retinyl citrate, 9-cis-retinyl ketoglutarate, 9-cis-retinyl fumarate, 9-cis-retinyl malate, and 9-cis-retinyl oxaloacetate.

8. The method of claim 7, wherein the synthetic retinal derivative is 9-cis-retinyl acetate or 9-cis-retinyl succinate.

9. The method of claim 1, wherein the synthetic retinal derivative is formulated as a tablet, pill, sachet, or capsule.

10. The method of claim 9, wherein said capsule is a hard or soft gelatin capsule.

11. The method of claim 1, wherein the synthetic retinal derivative is administered at a dose of about 0.1 to about 1000 mg.

12. The method of claim 1, wherein the synthetic retinal derivative is administered at a dose of about 0.01 to about 10 mg/kg body weight of the human subject.

13. The method of claim 12, wherein the synthetic retinal derivative is administered at a dose of about 0.05 to about 7.5 mg/kg body weight of the human subject.

14. The method of claim 13, wherein the synthetic retinal derivative is administered at a dose of about 0.1 to about 5 mg/kg body weight of the human subject.

15. The method of claim 14, wherein the synthetic retinal derivative is administered at a dose of about 0.1 to about 1 mg/kg body weight of the human subject.

16. The method of claim 1, wherein the synthetic retinal derivative is contained within a pharmaceutically acceptable vehicle, wherein the pharmaceutically acceptable vehicle is vegetable oil.

17. The method of claim 1, wherein the long term dosage regimen comprises administering an individual dosage greater than an effective daily dose.

18. The method of claim 1, wherein said human subject is an aging subject selected from at least 45 years of age, at least 50 years of age, at least 60 years of age, and at least 65 years of age.

19. The method of claim 1, wherein administering said synthetic retinal derivative restores or stabilizes photoreceptor function in the human subject with AMD.

20. The method of claim 1, wherein administering the synthetic retinal derivative restores or increases or stabilizes dark adaptation in the human subject with AMD.

21. The method of claim 1, wherein administering the synthetic retinal derivative increases or stabilizes contrast sensitivity in the human subject with AMD.

* * * * *